United States Patent [19]

Corbisier et al.

[11] Patent Number: 5,786,162

[45] Date of Patent: Jul. 28, 1998

[54] FUSED GENES AND THEIR USE FOR DETERMINING THE PRESENCE OF METALS OR OF XENOBIOTIC COMPOUNDS

[75] Inventors: Philippe Corbisier, Namur; Maximilien Mergeay, Retie; Ludovicus Diels, Oelegem, all of Belgium

[73] Assignee: Vito, Mol, Belgium

[21] Appl. No.: 469,775

[22] PCT Filed: Feb. 28, 1992

[86] PCT No.: PCT/EP92/00445

§ 371 Date: Dec. 27, 1993

§ 102(e) Date: Dec. 27, 1993

[87] PCT Pub. No.: WO92/15687

PCT Pub. Date: Sep. 17, 1993

Related U.S. Application Data

[63] Continuation of Ser. No. 108,754, Dec. 27, 1993, abandoned.

[30] Foreign Application Priority Data

Mar. 1, 1991 [WO] WIPO ............ PCT/EP91/00385

[51] Int. Cl.$^6$ ............ C12N 1/21; C12N 15/63; C12Q 1/66; C07H 21/04
[52] U.S. Cl. ............ 435/7.32; 435/6; 435/8; 435/172.3; 435/252.33; 435/320.1; 435/822; 435/829; 435/909; 536/23.2; 536/23.7; 536/23.1; 536/24.1; 935/72; 935/73
[58] Field of Search ............ 435/172.3, 252.3, 435/252.33, 320.1, 6, 8, 7.32, 822, 824, 909; 536/23.1, 23.2, 23.7, 24.1; 935/72, 73

[56] References Cited

FOREIGN PATENT DOCUMENTS

WO 90/08836  8/1990  WIPO.
   90/08836  9/1990  WIPO.

OTHER PUBLICATIONS

Boylan et al., Lux C, D and E Genes of the Vibrio Fischeri Luminescence Operon Code for the Reductase, Transferase, and Synthetase Enzymes Involved in Aldehyde Biosynthesis, *Chemical Abstracts*, 111, Abs. No. 91344q, 189 (1989).

Fernando et al., "Cloning and Expression of an Avian Metallothionein–Encoding Gene", *Gene*, 81, 177–183 (1989).

Furukawa et al., "Molecular Relationship of Chromosomal Genes Encoding Biphenyl/Polychlorinated Biphenyl Catabolism: Some Soil Bacteria Possess a Highly Conserved bph Operon", *Journal of Bacteriology*, 171, 5467–5472 (1989).

Nies et al., Journal of Bacteriology, 169(10):4865–4868, 1987.

Shields et al., Journal of Bacteriology, 163(3):882–889, 1985.

Nies et al., Journal of Bacteriology, 171(2):896–900, 1989.

Shaw et al., Molecular Plant–Microbe Interactions, 1(1):39–45, 1988.

Lampinen et al., Toxicity Assessment: An International Journal, 5:337–350, 1990.

forsman et al., Molecular General Genetics, 210:23–32, 1987.

Engenbrecht et al., Science, 227:1345–1347, 1985.

Schauer, TIBTECH, 6:23–27, 1988.

D. Nies, et al. *J. Bacteriol* 174: 8102 (1992).

*Primary Examiner*—Douglas W. Robinson
*Assistant Examiner*—Thanda Wai
*Attorney, Agent, or Firm*—Merchant, Gould, Smith, Edell, Welter & Schmidt, P.A.

[57] ABSTRACT

The invention relates to a fused gene containing: the promoter sequence of (a) gene(s) encoding the resistance to one or several metal(s) or encoding the catabolism of one or several xenobiotic compound(s), said promoter being inducible in the presence of said metal(s) or xenobiotic compound(s), or both, and downstream the promoter, a gene producing a detectable signal such as light emitting gene, said gene being under the control of said promoter, said gene producing a detectable signal being located at a position such that the induction of the promoter causes the transcription of the gene producing a detectable signal and such that there is no terminator between the promoter and the gene producing a detectable signal.

35 Claims, 13 Drawing Sheets

```
            10         20         30         40         50         60
5' GCCAGTGCCAAGCTTGCATGCCTGCAGGTCGACATGGACGGTCCATGTGTCTTCCTTTCA
3' CGGTCACGGTTCGAACGTACGGACGTCCAGCTGTACCTGCCAGGTACACAGAAGGAAAGT
            70         80         90        100        110        120
   ACGCAATATTGCGGACTCGGTCTGGTTTCTCGGCCTGTCGGTGGTCGTGGAGTCGTTTGA
   TGCGTTATAACGCCTGAGCCAGACCAAAGAGCCGGACAGCCACCAGCACCTCAGCAAACT
           130        140        150        160        170        180
   TCTGTTCCATGACGCCGGCGTCCTCCGGGCGGTCGTGACGCTTGCCTGATGCGGGCAACT
   AGACAAGGTACTGCGGCCGCAGGAGGCCCGCCAGCACTGCGAACGGACTACGCCCGTTGA
           190        200        210        220        230        240
   CCGCATACACGTACAGCCATGCACTACGCTCACGTCTCCGATTCTGTTGTCGAGAGCATG
   GGCGTATGTGCATGTCGGTACGTGATGCGAGTGCAGAGGCTAAGACAACAGCTCTCGTAC
           250        260        270        280        290        300
   CTCGTGATGCTGGTCGGCCTGATCGTCCTGTATGTGGGGTTCGCTGTCTATTTGCGGTGG
   GAGCACTACGACCAGCCGGACTAGCAGGACATACACCCCAAGCGACAGATAAACGCCACC
           310        320        330        340        350        360
   AAGCATGGGCCCGCCCCCAAGCGTAAGACTGAGTAGGGGCGAAAGCGGCACCCCAAAACG
   TTCGTACCCGGGCGGGGTTCGCATTCTGACTCATCCCCGCTTTCGCCGTGGGGTTTTGC
           370        380        390        400        410        420
   AGCAGGCGAAAGCGATAATCGTAATCTGCTCTTAATGCTGGTGATCGAGGATTCATGTAA
   TCGTCCGCTTTCGCTATTAGCATTAGACGAGAATTACGACCACTAGCTCCTAAGTACATT
           430        440        450        460        470        480
   ACTTCGGCGAGCGCCCAGCCGTTAGTACTTCAACCCCAAGCCCCCCGCACAGTCTCCCAA
   TGAAGCCGCTCGCGGGTCGGCAATCATGAAGTTGGGGTTCGGGGGGCGTGTCAGAGGGTT
           490        500        510        520        530        540
   GGAATGCGACGTTTCGTTCTGATCTTCGTGCTGCTCATTTGCCGTTCCAGTTTTCCTGGG
   CCTTACGCTGCAAAGCAAGACTAGAAGCACGACGAGTAAACGGCAAGGTCAAAAGGACCC
           550        560        570        580        590        600
   CGGCAGCGGCACGCTATTGTCAGCACGAGAAAGCCACGGCCACTTGGCACCTTGGGCACC
   GCCGTCGCCGTGCGATAACAGTCGTGCTCTTTCGGTGCCGGTGAACCGTGGAACCCGTGG
           610        620        630        640        650        660
   ACGAGCATCGTCATCAGCAGCCGGAAGGTAAAACGGATGCCGAGAAAAAGCCATTCGTGG
   TGCTCGTAGCAGTAGTCGTCGGCCTTCCATTTTGCCTACGGCTCTTTTTCGGTAAGCACC
           670        680        690        700        710        720
   ATACAGACTGCGGGTATGCCATCTGGTCTCCCTCCCGTTCGTCTATGGACAGACGCAGG
   TATGTCTGACGCCCCATACGGTAGACCAGAGGGAGGGCAAGCAGATACCTGTCTGCGTCC
           730        740        750        760        770        780
   ACGTGTTGATAGCGAATCGGGTAGAAGTGACCGATACTCAACATTCGTCCGAGTTCTCGT
   TGCACAACTATCGCTTAGCCCATCTTCACTGGCTATGAGTTGTAAGCAGGCTCAAGAGCA
           790        800        810        820        830        840
   CTCTGAATGCCAGGGCTCCCGACCGTCCTCAGTGGCAGCGTCTCGCTTGATCGGCGAGAC
   GAGACTTACGGTCCCGAGGGCTGGCAGGAGTCACCGTCGCAGAGCGAACTAGCCGCTCTG
           850        860        870        880
   GACGACTCTTTTTCTCCTTTCGTCTCTCGCCGAATTCACTGGC 3'
   CTGCTGAGAAAAAGAGGAAAGCAGAGAGCGGCTTAAGTGACCG 5'
```

→       FIG. 11

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 883 base pairs
        ( B ) TYPE: nucleic acid
        ( C ) STRANDEDNESS: double
        ( D ) TOPOLOGY: linear ( i i ) MOLECULE TYPE: Genomic DNA ( x i ) SEQUENCE DESCRIPTION: SEQ ID NO:1:

```
GCCAGTGCCA  AGCTTGCATG  CCTGCAGGTC  GACATGGACG  GTCCATGTGT  CTTCCTTTCA    60

ACGCAATATT  GCGGACTCGG  TCTGGTTTCT  CGGCCTGTCG  GTGGTCGTGG  AGTCGTTTGA   120

TCTGTTCCAT  GACGCCGGCG  TCCTCCGGGC  GGTCGTGACG  CTTGCCTGAT  GCGGGCAACT   180

CCGCATACAC  GTACAGCCAT  GCACTACGCT  CACGTCTCCG  ATTCTGTTGT  CGAGAGCATG   240

CTCGTGATGC  TGGTCGGCCT  GATCGTCCTG  TATGTGGGGT  TCGCTGTCTA  TTTGCGGTGG   300

AAGCATGGGC  CCGCCCCCAA  GCGTAAGACT  GAGTAGGGGC  GAAAGCGGCA  CCCCAAAACG   360

AGCAGGCGAA  AGCGATAATC  GTAATCTGCT  CTTAATGCTG  GTGATCGAGG  ATTCATGTAA   420

ACTTCGGCGA  GCGCCCAGCC  GTTAGTACTT  CAACCCCAAG  CCCCCCGCAC  AGTCTCCCAA   480

GGAATGCGAC  GTTTCGTTCT  GATCTTCGTG  CTGCTCATTT  GCCGTTCCAG  TTTTCCTGGG   540

CGGCAGCGGC  ACGCTATTGT  CAGCACGAGA  AAGCCACGGC  CACTTGGCAC  CTTGGGCACC   600

ACGAGCATCG  TCATCAGCAG  CCGGAAGGTA  AAACGGATGC  CGAGAAAAAG  CCATTCGTGG   660

ATACAGACTG  CGGGGTATGC  CATCTGGTCT  CCCTCCCGTT  CGTCTATGGA  CAGACGCAGG   720

ACGTGTTGAT  AGCGAATCGG  GTAGAAGTGA  CCGATACTCA  ACATTCGTCC  GAGTTCTCGT   780

CTCTGAATGC  CAGGGCTCCC  GACCGTCCTC  AGTGGCAGCG  TCTCGCTTGA  TCGGCGAGAC   840

GACGACTCTT  TTTCTCCTTT  CGTCTCTCGC  CGAATTCACT  GGC                      883
```

( 2 ) INFORMATION FOR SEQ ID NO:2:

( i ) SEQUENCE CHARACTERISTICS:
        ( A ) LENGTH: 883 base pairs ( B ) TYPE: nucleic acid
( C ) STRANDEDNESS: double
( D ) TOPOLOGY: linear ( i i ) MOLECULE TYPE: Genomic DNA ( x i ) SEQUENCE DESCRIPTION: SEQ ID NO:2:

| | | | | | |
|---|---|---|---|---|---|
| CGGTCACGGT | TCGAACGTAC | GGACGTCCAG | CTGTACCTGC | CAGGTACACA | GAAGGAAAGT | 60
| TGCGTTATAA | CGCCTGAGCC | AGACCAAAGA | GCCGGACAGC | CACCAGCACC | TCAGCAAACT | 120
| AGACAAGGTA | CTGCGGCCGC | AGGAGGCCCG | CCAGCACTGC | GAACGGACTA | CGCCCGTTGA | 180
| GGCGTATGTG | CATGTCGGTA | CGTGATGCGA | GTGCAGAGGC | TAAGACAACA | GCTCTCGTAC | 240
| GAGCACTACG | ACCAGCCGGA | CTAGCAGGAC | ATACACCCCA | AGCGACAGAT | AAACGCCACC | 300
| TTCGTACCCG | GGCGGGGGTT | CGCATTCTGA | CTCATCCCCG | CTTTCGCCGT | GGGGTTTTGC | 360
| TCGTCCGCTT | TCGCTATTAG | CATTAGACGA | GAATTACGAC | CACTAGCTCC | TAAGTACATT | 420
| TGAAGCCGCT | CGCGGGTCGG | CAATCATGAA | GTTGGGGTTC | GGGGGGCGTG | TCAGAGGGTT | 480
| CCTTACGCTG | CAAAGCAAGA | CTAGAAGCAC | GACGAGTAAA | CGGCAAGGTC | AAAAGGACCC | 540
| GCCGTCGCCG | TGCGATAACA | GTCGTGCTCT | TTCGGTGCCG | GTGAACCGTG | GAACCCGTGG | 600
| TGCTCGTAGC | AGTAGTCGTC | GGCCTTCCAT | TTTGCCTACG | GCTCTTTTC | GGTAAGCACC | 660
| TATGTCTGAC | GCCCCATACG | GTAGACCAGA | GGGAGGGCAA | GCAGATACCT | GTCTGCGTCC | 720
| TGCACAACTA | TCGCTTAGCC | CATCTTCACT | GGCTATGAGT | TGTAAGCAGG | CTCAAGAGCA | 780
| GAGACTTACG | GTCCGAGGG | CTGGCAGGAG | TCACCGTCGC | AGAGCGAACT | AGCCGCTCTG | 840
| CTGCTGAGAA | AAAGAGGAAA | GCAGAGAGCG | GCTTAAGTGA | CCG | | 883

FUSED GENES AND THEIR USE FOR DETERMINING THE PRESENCE OF METALS OR OF XENOBIOTIC COMPOUNDS

CROSS-REFERENCE TO RELATED APPLICATIONS

The present application is a file wrapper continuing application of U.S. Ser. No. 08/108,754 filed Dec. 27, 1993 now abandoned, application Ser. No. 08/108,754 is a national stage application of PCT application Ser. No. PCT/EP92/00445 filed 28 Feb. 1992 and published as WO 92/15687 on 17 Sep. 1992.

The invention relates to fused genes, vectors containing them, process for preparing them and their use for determining the presence of metals or of xenobiotic compounds.

Toxical wastes are a significant contamination problem for a range of industries.

Among the substances involved, one may cite heavy metals and xenobiotic compounds which are very polluting and which may endanger health. The sources of pollution are varied. Moreover, with the enforcement of strict regulations, in order to limit the wastes containing metals such as heavy metals and xenobiotic compounds, there is a need for methods of detection of metals and xenobiotic compounds in environment.

Most of the methods used routinely to measure metal concentrations are physical methods which rely on the substantial physical (usually electronic) differences between the metal and the carrier medium.

Among these methods, the most commonly used are the inductively coupled plasma systems, the X-ray fluorescence or the atomic absorption.

The main advantage of these methods is the very low limits of detection (about 0.1 ppm) as well as a multielementary aspect of the analysis. But, the main drawbacks are the high price of the equipment, the use of which requires high qualified people, the long time required for preparing the samples to be analyzed and the sensitivity of these methods related to many interferences due to the nature of the samples.

Many organisms can tolerate high concentrations of heavy metals such as cadmium and lead. The mechanism involved varies. Specific, genetically coded resistance to heavy metals can evolve in populations of organisms exposed over long periods of time to heavy metals ("Genetic adaptation to heavy metals in aquatic organisms: a review" P. L. Klerks, J. S. Weis (1987), Environmental pollution 45: 173–205). Searches of soil in sites heavily contaminated with heavy metals routinely reveal strains of microorganisms with enhanced abilities to tolerate heavy metals. Several such strains have been isolated from a heavily contaminated site in Belgium, and the genetics of their responses to heavy metals have been analyzed ("*Alcaligenes eutrophus* CH34 is a facultative chemilithotroph with plasmid-bound resistance to heavy metals" M. Mergeay, D. Nies, H. G. Schlegel, J. Gerits, P. Charles, F. van Gijsegem (1985), J. Bacteriol. 162: 328–334; "Cloning of plasmid genes encoding resistance to cadmium, zinc, and cobalt in *Alcaligenes eutrophus* CH34" D. Nies, M. Mergeay, B. Friedrich, H. G. Schlegel (1987), J. Bacteriol. 169:4865–4868).

Most microorganisms can degrade a wide variety of compounds to generate metabolic energy and to make available metabolic intermediates, and particularly carbon, for their use. Some organisms specialize in the degradation of exotic materials, using unusual enzyme systems to do so. These are frequently soil bacteria that have evolved in sites where industrial activity has released a substantial amount of such material into the soil. The ability to degrade highly conjugated aromatic hydrocarbons and their halide derivatives is a good example, as these materials are rarely found in nature and require special enzymes to initiate their degradation, usually by oxygenation.

*Alcaligenes eutrophus*, as a bacterial organism, presents specific inducible genes of resistance with respect to heavy metals or involved in the catabolism of xenobiotics such as PCBs.

The bacteria of the group of *Alcaligenes eutrophus* (gram negative) have beside the property of being facultative chemilithotroph, the property of comprising one of several megaplasmids which confer on them multiple resistances with respect to heavy metals. These bacteria have been discovered in the neighborhood of non ferrous metal factories and in the neighborhood of mining sites in Belgium and in Zaire (Diels et al., 1988(a), Isolation and characterization of resistant bacteria to heavy metals from mining areas of Zaire. Arch. Int. Physiol. Biochim. 96(2) B83; Diels et al., 1988(b), Detection of heterotrophic bacteria with plasmid-bound resistances to heavy metals from Belgian industrial sites. Arch. Int. Physiol. Biochim. 96(2)B84).

*Alcaligenes eutrophus* CH34 (ATCC 43123) presents two megaplasmids: pMOL28 (165 kb) and pMOL30 (240 kb). pMOL30 has been found to be involved in the expression of heavy metal resistance to cadmium, zinc, cobalt, copper, lead, mercury, thallium and manganese. pMOL28 has been found to be involved in the expression of heavy metal resistance to cobalt, chromium, thallium and mercury (Mergeay et al., 1985, *Alcaligenes eutrophus* CH34 is a facultative chemilithotroph with plasmid-bound resistance to heavy metals. J. Bacteriol. 169, 328–334; Nies et al., 1987, Cloning plasmid genes coding resistance to cadmium, zinc and cobalt in *Alcaligenes eutrophus* CH34. J. Bacteriol. 169, 4865–4868; Diels et al. 1989(a), Large plasmid governing multiple resistance to heavy metals: a genetic approach. Toxicol. Environ. Chem. 23, 79–89).

These megaplasmids are transmissible by homologous crossings (Mergeay et al., 1985, *Alcaligenes eutrophus* CH34 is a facultative chemilithotroph with plasmid-bound resistance to heavy metals. J. Bacteriol. 169, 328–334, Table 1).

The restriction map of the native plasmids of *Alcaligenes eutrophus*, the locus of the various resistance with respect to heavy metals as well as resistance mechanism for some metals (mercury, cadmium, zinc, nickel, cobalt, chromium) start to be understood.

pMOL30, for instance, contains an EcoRI fragment of 9.1 kb which is named czc, which has been evidenced by cloning and which confers simultaneously a resistance to cadmium, zinc and cobalt ions (Nies et al., 1987, Cloning plasmid genes coding resistance to cadmium, zinc and cobalt in *Alcaligenes eutrophus* CH34. J. Bacteriol. 169, 4865–4868).

In the case of cadmium, cobalt, nickel and zinc, the resistance is determined by an efflux system (expulsion of the metallic cations after their entry into the cell). Besides, an accumulation of the metal seems to take place at the level of the bacterial envelops further to an alcalinisation of the culture medium by the bacteria themselves (Diels et al., 1989(b), Accumulation of Cd and zinc ions by *Alcaligenes eutrophus* strains. Biohydrometallury 89, Jackson Hale USA). This phenomenon of accumulation takes place at the stationary phase and depends on the conditions of metabolism.

Gene and protein fusions have been instrumental in the study of gene regulation, protein processing, export and other aspects of gene function.

All reporter gene systems in current use involve genes that encode an enzymatically active protein. The sensitivity of these systems varies according to the properties of the reporter enzyme, the nature and quality of the available assays and the presence or absence of interfering activities in the cell type. The lactose (lac) operon of *Escherichia coli* has been employed most extensively in these studies because a great amount of information is available regarding various aspects of this genetic system (Berman M. L. 1983, "Vectors for constructing hybrid genes" Biotechniques 1:178-183; Koenen et al. 1982, "Immunoenzymatic detection of expresses gene fragments coled in the lacZ gene of *E. coli*. J. Bacteriol. 1:509-512; Silhavy et al., 1985, Uses of lac fusions for the study of biological problems. Microbiol. Rev. 49, 398-418; Silhavy et al., 1984, "Experiments with gene fusions" Cold Spring Harbor Laboratory. Cold Spring Harbor, N.Y.).

A number of plasmid vectors have been designed for the purpose of cloning and the subsequent evaluation of lac gene with promoter activity (Casadaban et al., 1980, "In vitro gene fusions that join an enzymatically active beta-galactosidase segment to amino-terminal fragments of exogenous proteins: *Escherichia coli* plasmid vectors for the detection and cloning of translational initiation signals" J. Bacteriol. 143:971-980; Shapira et al., 1983, "New versatile plasmid vectors for expression of hybrid proteins coded by a cloned gene fused to lacZ gene sequences encoding enzymatically active carboxyterminal portion of beta-galactosidase" Gene 25:71-82; Minton N. P., 1984, "Improved plasmid vectors for the isolation of translational lac gene fusions" Gene 31:269-273) or for the study of protein function. They utilize gene transcription and translation initiation signals and result in enzymatically active β-galactosidase proteins containing amino-terminal amino acid sequences from the exogenous gene (Müller-Hill et al., 1976, "Repressor-galactosidase chimaeras in Markam R. and Horne R. W. (eds) Structure-function relationship of proteins" North-Holland, New York, pp. 167-179; Bassford et al., 1978, "Genetic fusions of the lac operon: a new approach to the study of biological process in Miller J. H. and Reznikoff W. S. (eds) The operon" Cold Spring Harbor Laboratory, Cold Spring Harbor, N.Y., pp. 245-261; Guarente et al., 1980, "Improved methods for maximizing expression of a cloned gene: bacterium that synthesizes rabbit beta-globin" Cell 20:543-553).

These hybrid proteins have been purified readily by following their β-galactosidase activity and used for determining amino-terminal functional domains of proteins (Müller-Hill et al., 1976, "Repressor-galactosidase chimaeras in Markam R. and Horne R. W. (eds) Structure-function relationship of proteins" North-Holland, New York, pp. 167-179; Silhavy et al., 1976, "Conversion of beta-galactosidase to a membrane-bound state by gene fusion" Proc. Natl. Acad. Sci. USA 73:3423-3427; Hall M. et al., 1981, "Gene analysis of the major outer membrane proteins of *Escherichia coli* in Roman H. L., Campbell A., and Sandler L. M. (eds)" Annual Reviews of Genetics, vol. 15, Annual Reviews, Palo Alto Calif. 91-142) and for eliciting antibody formation against amino-terminal antigenic determinants (Schuman et al., 1988, "Labeling of proteins with beta-galactosidase by gene fusion identification of a cytoplasmic membrane component of *Escherichia coli* maltose transport system" J. Chem. 225:168-174).

Another reporter gene is the luciferase reporter gene. Bacterial luciferase enzymes catalyze a light emitting reaction in luminous bacteria. The light emitting luciferase catalyzed reaction is as follows:

$RCHO+O_2+FMNH_2 \rightarrow RCOOH+FMN+H_2O+photon$ (490 nm)

in which R is an aliphatic moiety containing at least seven carbon atoms, preferably from 7 to 14 carbon atoms, FMN is a flavin mononucleotide and $FMNH_2$ is reduced flavin mononucleotide (Meighen E. A., 1988, "Enzymes and genes from the lux operon of bioluminescent bacteria" Ann. Rev. Microbiol. 42:151-176).

In bacteria, the oxidized flavin is efficiently reduced and continuously available to cytoplasmic enzymes, such as luciferase.

Upon external addition of the aldehyde substrate, which instantly penetrates living cells, the activity of luciferase can be followed in vivo by measuring light emission. Light can be monitored by a number of methods and with high sensitivity. Since a bacterial luciferase molecule gives rise to about one photon in the luciferase reaction, as little as 10 luciferase molecules can be detected by a luminometer (Olsson O. et al., 1988, "The use of the luxA gene of the bacterial luciferase operon as a reporter gene", Mol. Gen. Genet. 215:1-9).

The luciferase gene cluster from the marine microorganisms *Vibrio fischeri*, the luxAB structural genes from V. harveyi and the firefly cDNA from *Photinus pyralis* have recently been introduced as reporter genes in procaryotic (Engebrecht J. et al., 1985, "Measuring gene expression with light" Sciences 227:1345-1347; Legocki R. P. et al., 1986, "Bioluminescence in soybean root nodules: Demonstration of a general approach to assay gene expression in vivo by using bacterial luciferases" Proc. Natl. Acad. Sci. USA 83:9080-9084; Karp M. T. et al., 1986, "Continous in vivo monitoring of gene expression using cloned bacterial luciferase genes" Biolum. Chemil. pp. 385-389; Schmetterer G. et al., 1986, "Expression of luciferases from *Vibrio harveyi* and *Vibrio fischeri* in filamentous cyanobacteria. J. Bacteriol. 167:411-414; Carmi O. A. et al., 1987, "Use of bacterial luciferases to establish a promoter probe vehicle capable of non destructive real-time analysis of gene expression in Bacillus" spp. J. Bacteriol. 169:2165-2170; Nussbaum A. et al., 1989, "Use of a bioluminescence gene reporter for the investigation of a red-dependent and gram-dependent plasmid recombination i: *Escherichia coli* K12" J. Mol. Biol. 203:402) as well as in eucaryotic organisms (Ow D. W. et al., 1986, "Transcient and stable expression of the firefly luciferase gene in plant cells and transgenic plants" Science 234:856-859; Dewet J. R. et al., 1985, "Cloning of firefly luciferase cDNA and expression of active luciferase in *E. coli*" Proc. Natl. Acad. Sci. USA 82:7870-7873; Williams T. M. et al., 1989, "Advantages of firefly luciferase as reporter gene: application to the interleukin-2 gene promoter", Anal. Biochem. 176:28-32; Riggs C. D. et al. 1987, "Luciferase reporter gene cassettes for plant gene expression studies" Nucleic Acids Res. 15:8115; Dilella G. A. et al., 1987, "Utility of firefly luciferase as reporter gene for promoter activity in transgenic mice" Nucl. Acids Res. 16:4159).

The firefly luciferase enzyme catalyses the ATP-dependent oxidation of a high molecular weight substrate, luciferin (Deluca et al., 1978, Purification and properties of firefly luciferase. Methods Enzymol. 57, 3-15; Mc Elroy et al., 1985, Firefly luminescence, p. 387-399 in J. G. Burr (ed.) Chemibioluminescence, Marcel Dekker Inc., New York). This substance is only slowly transported through cell membranes, in contrast to the aldehyde substrate in the bacterial reaction.

The Journal of Biotechnology (September 1990, p.4749–4757, Burlage, Sayler and Larimer) describes the fusion of the lux genes of *Vibrio fischeri* to a fragment from plasmid NAH7, containing the promoter for the upper pathway of degradation of naphthalene (related to some naturally occuring compounds) and the first three cistrons of the nahA gene. A Pseudomonas strain (gram negative bacterium) containing this construction is inducible to high levels of light production in the presence of a suitable substrate.

Molecular Biology (1989), 3(8), p. 1011–1023, describes the coupling of the proU to luxAB, proU being the promoter of a gene regulating osmolarity in *Salmonella typhimurium*; the above plasmid thus obtained is cloned in *E. coli* and is used to monitor in vivo real time kinetics of proU induction following osmotic shock.

The aim of the invention is to provide with a process for detecting the presence of metals or xenobiotic compounds said process being sensitive, cheap, simple and being suitable for an automatic or field use.

The aim of the invention is to provide with a method for detecting the presence of metals or xenobiotic compounds, requiring no expensive and no massive capital equipment and low operator intervention.

The aim of the invention is also to provide with a method enabling to give a positive reply (light emission) in the presence of a metal or a xenobiotic compound.

Another aim of the invention is to provide with a method for detecting the presence of metals and/or xenobiotic compounds which is specific for the metal or the xenobiotic compound which is to be detected.

The invention relates to a fused gene containing:

the promoter sequence of (a) gene(s) encoding the resistance to one or several metal(s) or encoding the catabolism of one or several xenobiotic compound(s), said promoter being inducible in the presence of said metal(s) or xenobiotic compound(s), or both, and downstream the promoter, a gene producing a detectable signal such as light emitting gene, said gene being under the control of said promoter, said gene producing a detectable signal being located at a position such that the induction of the promoter causes the transcription of the gene producing a detectable signal and such that there is no terminator between the promoter and the gene producing a detectable signal, said gene being such that it enables to recycle fatty acid (which has been generated during the reaction responsible for the detectable signal) into aldehyde.

The expression "the gene producing a detectable signal being under the control of the promoter" means that the promoter of the gene producing a detectable signal has been deleted.

By metal, one designates the transition metals, the rare earth, the elements having metallic properties in the families IIIa, IVa, Va and VIa of the Mendelieff table.

By metals, one may cite for example cadmium, zinc, cobalt, copper, lead, mercury, thallium, chromium and manganese under the form of salts, either in a soluble or non soluble state.

The expression "inducible promoter in the presence of said metal" means that there is a minimum concentration of said metal under which the promoter is not induced. This depends particularly upon the nature of the promoter region and its regulation, the accessibility of the metal to the promoter region, the nature and the solubility of the metal.

The xenobiotic compounds designate the compounds which may endanger health and which are man made chemicals (non naturally occurring compounds). By way of example, one may cite fungicides, herbicides, pesticides, insecticides, chloroorganic compounds, particularly biphenyl compounds.

In the following, the expression "resistance gene" corresponds to the gene responsible for the resistance to one or several metals and the expression "catabolism gene" corresponds to the gene responsible for the catabolism of one or several xenobiotic compounds.

The fused genes of the invention are placed in a host cell, e.g. bacteria, for the production of light to occur.

In the bioluminescent cell, the reaction of light production takes place with the oxidation of long chained aldehydes and of reduced mononucleotide flavine ($FMNH_2$). The energy source of this reaction is given by the transformation of aldehyde (RCHO) into its corresponding fatty acid (RCOOH) according to the following reaction:

$$RCHO + FMNH_2 + O_2 \rightarrow RCOOH + FMN + H_2O + h\nu.$$

RCHO representing an aldehyde from 7 to 14 carbon atoms.

The reaction always occurs because there is always a small amount of aldehyde in the host cell.

When there is no more aldehyde in the host cell, it is necessary to add extra aldehyde, to obtain the production of light. However, aldehyde has the drawback of being toxic and besides, in this system, there is accumulation of fatty acid, which is stored by the host cell and is toxic in the long run.

Besides, the light production depends on the added exogenous aldehyde.

In order to avoid these drawbacks, the gene which produces the detectable signal is such that it is liable to recycle fatty acid into aldehyde according to the following reaction:

$$RCOOH + NADPH_2 + ATP \rightarrow RCHO + NADP + AMP + PPi.$$

This avoids the use of exogenous aldehyde and this prevents fatty acid from being accumulated in the host cell.

It may be possible to make a luminescence test which responds to several analytes with different signals. The *Vibrio fischeri* genes (giving green light) could be used to detect an analyte (for example: a metal) and a different luciferase gene producing light of slightly different wavelengths (for instance: lux beetle luciferese which gives red light) in another fusion would detect another analyte (for example: a xenobiotic or another metal). If more genes have different signals, it would be possible to distinguish, in principle, the different analytes within the same bacteria.

According to another embodiment of the invention, the fused gene contains beside the inducible promoter also the coding sequence of the gene responsible for the resistance to one or several metals or responsible for the catabolism of one or several xenobiotic compounds.

When the fused gene does not contain the coding sequence of the gene responsible for the resistance to one or several metals or responsible for the catabolism of one or several xenobiotic compounds, this embodiment is very sensitive to metal or xenobiotics.

When the fused gene contains the coding sequence of the gene responsible for the resistance to one or several metals or responsible for the catabolism of one or several xenobiotic compounds, the embodiment is less sensitive to metal or xenobiotics, but enables to measure concentrations of metal or xenobiotics higher than the lethal ones.

In this case (i.e. when the coding part of the gene responsible for the resistance of a metal—or for the catabolism of a xenobiotic—is present), there might be translation of the resistance gene or of the catabolism gene, if the translation machinery can be operated in the host cell.

Translation of the resistance gene or of the catabolism gene might be required if the concentration of the metal or of the xenobiotic compound to be measured is higher than the lethal concentration of said metal or of said xenobiotic compound for the host cell containing the fused gene.

The invention also relates to a fused gene wherein the gene producing a detectable signal
- either is located downstream the promoter and upstream the gene encoding the resistance or the catabolism,
- or is located downstream the promoter and downstream the gene encoding the resistance or the catabolism,
- or is located downstream the promoter and in the gene encoding the resistance or the catabolism.

When the fused gene contains only the inducible part of the resistance gene or of the catabolism gene without the coding sequence of said gene, the gene producing the detectable signal is downstream the promoter, and can be spaced by a base pair sequence the length of which is such that the gene producing a detectable signal is still induced by the promoter.

When the fused gene contains, beside the promoter of the resistance gene or of the catabolism gene, also the coding part of said gene, the gene producing the detectable signal can be
- downstream the promoter and upstream the gene encoding resistance or catabolism (i.e. between the inducible promoter and the coding part of the resistance gene or catabolism gene),
- or can be downstream the coding part of the resistance gene or of the catabolism gene,
- or within the gene encoding resistance or catabolism.

When the gene producing the signal is located downstream the coding part of the gene encoding resistance or catabolism, the promoter must be strong enough to provoke the transcription of the gene producing the signal.

The strength of a promoter is defined by the ability to induce the transcription of genes which are remote from the promoter.

When the gene producing the signal is located within the coding part of the resistance gene, or of the catabolism gene, there might be transcription and translation of the resistance gene, or of the catabolism gene, if the resistance gene, or catabolism gene, is not damaged by the insert containing the gene producing the signal, or, there might be partial transcription and partial translation of the resistance gene or of the catabolism gene.

When the gene producing the signal is located within the inducible promoter, the gene producing the signal is no more under the control of the inducible promoter.

The invention also relates to a fused gene wherein a termination sequence is located immediately upstream the promoter.

This termination sequence enables to avoid any interference transcription by other upstream promoters and would increase the ratio signal/noise by lowering the expression of the light emitted by the bacteria in the absence of metals or of xenobiotic compounds.

According to an advantageous embodiment of the invention, the gene producing a detectable signal is the luciferase gene.

Luciferase is interesting for the following reasons:
1) extremely low levels of light can be accurately measured, and light can be quantified linearly over many orders of magnitude;
2) there is no significant endogenous background activity (as there is with β-galactosidase, for example)
3) transcription can be monitored non-invasively over time in vitro, in liquid or in a natural habitat, because the repeated application of the substrate (luciferin or n-decanal) is generally non-toxic;
4) the assays are very simple and inexpensive;
5) Light does not diffuse or accumulate in situ; the source of gene expression can be localized spatially with high resolution.

The luciferase gene can originate from *Vibrio fischeri* or from *Vibrio harveyi* or from *Photobacterium phosphoreum* or from *Xenorhabdus luminescens*.

A preferred luciferase gene is the one originating from *Xenorhabdus luminescence*, cloned in *E. coli* (Frackman S. et al., 1990, "Cloning, Organization and expression of the bioluminescence genes of *Xenorhabdus luminescens*" J. Bact. 172:5767–5773).

A preferred luciferase gene is the one originating from *V. fischeri*; the sequence which is responsible for regulation as well as the expression of bioluminescence as well as the synthesis of enzymes implied in the bioluminescence are known (see Devine et al., 1988, Nucleotide sequence of the lux R and lux I genes and structure of the primary regulatory region of lux regulon of *V. fischeri* ATCC 7744. Biochem. 27, 837–842; Engebrecht et al., 1986).

Five gene lux A, B, C, D, E, respectively code for a subunit α and β of luciferase, a fatty reductase, an acyltransferase and an acylprotein synthase. Those enzymes enable oxidation of aldehyde into fatty acid with production of photons. The aldehyde is then recycled by reduction of the fatty acid which has been formed.

The genes lux A, B, C, D, E, have been cloned without their regulon luxR and luxI forming thus an operon without the promoter and which is called lux cassette (Schaw J. J. et al., 1988, "Transposon Tn4431 mutagenesis of *Xanthonomas campestris* pv *campestris*; characterization of a non-pathogenic mutant and cloning of a locus for pathogenicity" Mol. Plant-Microbe Interaction. 1:39–45).

According to another embodiment of the invention, the gene encoding resistance to a metal or encoding the catabolism of a xenobiotic compound originates from bacteria of the *Alcaligenes eutrophus* type.

The invention also relates to a fused gene, wherein:
the promoter and the gene encoding resistance is a promoter and a gene encoding resistance to zinc, obtained from pBR325 containing the czc fragment of pMOL30 from *Alcaligenes eutrophus* strain CH34 and surrounding EcoRI fragment, digested with SalI, said promoter and gene encoding resistance is at the multiple cloning site of the plasmid pUCD615, said plasmid containing the lux operon of *Vibrio fischeri*.

The invention also relates to a fused gene, wherein:
the promoter and the gene encoding resistance is the promoter and gene encoding resistance to cobalt, obtained from pBR325 containing czc fragment of pMOL30 from *Alcaligenes eutrophus* strain CH34 digested with EcoRI-PstI, said promoter and gene encoding resistance is at the multiple cloning site of the plasmid pUCD615, said plasmid containing the lux operon of *Vibrio fischeri*.

The invention also relates to a recombinant vector, particularly for cloning and/or expression, comprising a vector sequence, notably of the type plasmid, cosmid or phage and a fused gene according to the invention, in one of the non essential sites for its replication.

The invention also relates to a recombinant vector containing in one of its non essential sites for its replication, necessary elements to promote, in a cellular host transcription and translation of the gene producing a detectable signal and transcription, and possibly translation, of the gene responsible for the resistance to a metal or responsible for the catabolism of a xenobiotic compound, and in addition to the inducible promoter possibly a signal sequence and/or anchoring sequence.

The invention also relates to a cellular host, notably *E. coli*, transformed by a recombinant vector according to the invention, or *Alcaligenes eutrophus*, transconjugated by a recombinant vector according to the invention, and comprising the regulation elements enabling the expression of the gene producing a detectable signal and possibly the expression of the gene encoding resistance to a metal or encoding the catabolism of a xenobiotic compound.

An advantageous cellular host of the invention is *E. coli* transformed by a fused gene wherein the promoter and the gene encoding resistance is a promoter and a gene encoding resistance to zinc, obtained from pBR325 containing the czc fragment of pMOL30 from *Alcaligenes eutrophus* strain CH34 and surrounding EcoRI fragment, digested with SalI, said promoter and gene encoding resistance is at the multiple cloning site of the plasmid pUCD615, said plasmid containing the lux operon of *Vibrio fischeri*.

This cellular host forms a biosensor enabling to detect a range of about 10 to about 65 ppm of zinc, and preferably as little as 0.1 ppm.

Another advantageous cellular host of the invention is *E. coli* transformed by a fused gene wherein:

the promoter and the gene encoding resistance is the promoter and gene encoding resistance to cobalt, obtained from pBR325 containing czc fragment of pMOL30 from *Alcaligenes eutrophus* strain CH34 digested with EcoRI-PstI, said promoter and gene encoding resistance is at the multiple cloning site of the plasmid pUCD615, said plasmid containing the lux operon of *Vibrio fischeri*.

This cellular host forms a biosensor enabling to detect a range of about 30 to about 120 ppm of cobalt, and preferably as little as 0.1 ppm.

Another advantageous cellular host of the invention is *Alcaligenes eutrophus* obtained by the conjugation of *Alcaligenes eutrophus* and *E. coli*, *E. coli* containing the vector pUCD623, itself containing a transposon Tn4431 which is Tn21 transposon containing the tetracycline resistance and the lux operon of *Vibrio fischeri* without its own promoter, the selection of the obtained transconjugants carried out on tetracycline plates, the replication of the transconjugants on media with different concentrations of metals, the detection of the light producing transconjugants being then carried out.

Another advantageous cellular host of the invention is *Alcaligenes eutrophus*, obtained by conjugation of *Alcaligenes eutrophus* and of *E. coli* strain CM601, which gives AE714, transferred into A5.3 to give AE859, which gives light expression in the presence of chromium.

This cellular host forms a biosensor enabling to detect a range of about 20 to about 60 ppm of chromium, and preferably as little as 0.1 ppm.

Another advantageous cellular host of the invention is *Alcaligenes eutrophus*, obtained by conjugation of *Alcaligenes eutrophus* and of *E. coli* strain CM601, which gives AE453, transferred into A5.3 to give AE891, which gives light expression in the presence of nickel.

This cellular host forms a biosensor enabling to detect a range of about 5 to about 120 ppm of nickel, and preferably as little as 0.1 ppm.

Another advantageous cellular host of the invention is *Alcaligenes eutrophus*, obtained by conjugation of *Alcaligenes eutrophus* and of *E. coli* strain CM601, which gives AE866, which gives light expression in the presence of copper.

This cellular host forms a biosensor enabling to detect a range of about 1 to about 100 ppm of copper, and preferably as little as 0.1 ppm.

Another advantageous cellular host of the invention is *Alcaligenes eutrophus*, obtained by conjugation of *Alcaligenes eutrophus* and of *E. coli* strain CM601, which gives AE890, which gives light expression in the presence of copper and cannot grow on minimal plates containing lead.

Another advantageous cellular host of the invention is *Alcaligenes eutrophus*, obtained by conjugation of *Alcaligenes eutrophus* and of *E. coli* strain CM601, which gives A5.23 or A5.24, which gives light expression in the presence of biphenyl compounds.

This cellular host forms a biosensor enabling to detect a range of about 10 ppm, preferably as little as 1 ppb of biphenyl compounds, such as 4-chloro-biphenyl.

The invention also relates to a process for in vitro preparing a cellular host containing a fused gene comprising the following steps:

determination of the promoter and the gene encoding resistance to one or several metals or encoding the catabolism of one or several xenobiotic compounds and isolation of the corresponding nucleic acid fragment of said promoter and gene, said promoter and gene comprising possibly a marker of the presence of the gene, fusing said nucleic fragment with a gene producing a signal deleted from its own promoter, said gene producing a signal comprising possibly a marker of the presence of the gene, introducing the result of above-mentioned fusion into a cellular host, such as *E. coli*, possibly selecting the cellular host with the marker(s) placed in a medium where the marker(s) can be detected, detecting light producing cellular hosts placed in an appropriate medium containing one or several metal(s) or a xenobiotic compound.

The invention also relates to a process for preparing a cellular host emitting light in the presence of zinc, wherein:

the promoter and the gene encoding resistance is a promoter and a gene encoding resistance to zinc, obtained from pBR325 containing the czc fragment of pMOL30 from *Alcaligenes eutrophus* strain CH34 and surrounding EcoRI fragment, digested with SalI, the result of the digestion is inserted into the plasmid pUCD615, at its multiple cloning site, and containing the lux operon of *Vibrio fischeri*, the result of said insertion is cloned into *E. coli*, a selection is carried out on ampicillin plates with various concentrations of zinc, the detection of the light producing *E. coli* in the presence of zinc is carried out.

The invention also relates to a process for preparing a cellular host emitting light in the presence of cobalt, wherein:

the promoter and the gene encoding resistance is the promoter and gene encoding resistance to cobalt, obtained from pBR325 containing czc fragment of pMOL30 from *Alcaligenes eutrophus* strain CH34 digested with EcoRI-PstI, the result of the digestion is inserted into the plasmid pUCD615, as its multiple cloning sites, containing the lux operon of *Vibrio fischeri*, the result of said insertion is cloned into *E. coli*, the selection is carried out on ampicillin plates with various concentrations of cobalt, the detection of the light producing *E. coli* in the presence of cobalt is carried out.

The invention also relates to a process for in vivo preparing a cellular host containing a fused gene comprising the following steps:

conjugation, to obtain transconjugants, of a cellular host containing a promoter and a gene encoding the resistance to a metal or encoding the catabolism of a xenobiotic compound and possibly a marker of the presence of the gene, with another cellular host containing a transposon containing the gene emitting the detectable signal without its own promoter and possibly a marker of the presence of said gene, recovery of the transconjugants, possible selection of transconjugants with the marker(s) placed in a medium where the marker(s) can be detected, possible application of transconjugants on media with different concentrations of metal or xenobiotics, selection of transconjugants emitting light in the presence of a medium containing a metal or a xenobiotic compound.

A preferred process for in vivo preparing a cellular host containing fused gene comprises the following steps:

the conjugation, to obtain transconjugants, of a cellular host containing a promoter and a gene encoding the resistance to a metal or encoding the catabolism of a xenobiotic compound with another cellular host containing a transposon containing the gene emitting the detectable signal without its own promoter and a marker of the presence of said gene, said marker being advantageously tetracycline, the recovery of the cellular host containing said promoter and said gene encoding the resistance to a metal or encoding the catabolism of a xenobiotic compound with elimination of the cellular host containing said transposon, by means of the marker and by means of a minimum medium culture enabling the selection of only the cellular host containing said promoter and said gene encoding the resistance to a metal or encoding the catabolism of a xenobiotic compound, the application of the abovesaid transconjugants on media containing or not the metal or xenobiotic compound, to select the transconjugants emitting light only in the presence of a specific heavy metal or in the presence of a specific xenobiotic compound.

For instance, when the cellular host containing said promoter and said gene encoding the resistance to a heavy metal or to a xenobiotic compound is *Alcaligenes eutrophus* and when the cellular host containing the transposon is *E. coli* CM601 (containing transposon Tn4431), the resistance to tetracycline enables to select on the one hand *Alcaligenes eutrophus* in which Tn4431 transposon has been inserted and on the other hand strain CM601 which contains said transposon.

A minimum medium:

284 gluconate or

Schatz azelate, on which CM601 cannot live because CM601 strains originates from HB101, autotrophic for leucine and proline, which enables to select only *Alcaligenes eutrophus*.

284 gluconate medium is as follows:

the basic composition of this culture medium is described in "*Alcaligenes eutrophus* CH34 is a facultative chemilithotroph with plasmid-bound resistance to heavy metals" M. Mergeay et al. (1985), J. Bacteriol. 162: 328–334; gluconate (0.2%) is used as carbon source).

Schatz azelate is described in Schatz A. et al. (1952) "Growth and hydrogenase activity of a new bacterium", *Hydrogenomonas facilis*. J. Bacteriol. 63:87–98; the carbon source which is used is azelate (0.2%)).

As the transposon can be inserted anywhere in the genome of *Alcaligenes eutrophus*, it is necessary to select the transconjugants in which the transposon is inserted at a right place.

For this purpose, a film is deposited on the dishes containing the transconjugants on said minimum medium, with or without a heavy metal or a xenobiotic compound. This technique enables to select the constitutive conjugations (light emission independent on the presence of metal) from the non-specific inducible fusions (light emission in the presence of one or several metals or under particular stress conditions) from the specific inducible fusions (light emission in the presence of a specific metal).

The detection of bacteria which have lost their resistance is also carried out on minimum medium in the presence of metals. This loss or decrease in the resistance is due either because of an insertion of said transposon in the resistance gene or in its promoter or because of the loss of the plasmid carrying the resistance or a part of the plasmid.

More precisely, the in vivo fusion can be carried out as follows:

1) The strains CM601 and the strains presenting resistances with respect to metals and/or xenobiotic compounds are cultured in a liquid medium in 5 ml of medium 869 for 16 h under stirring at 30° C. Medium 869 is equivalent to Luria-Broth medium: for 1 l of milli-q water:

10 q NaCl 5 g Bacto-Yeast extract 10 g Bacto-tryptone adjust pH to 7.5 with sodium hydroxide.

2) 100 µl of culture are deposited on an agar dish (medium 869) in such a way that the strains CM601 are deposited on one third of the dish, the strains presenting resistance are deposited on a second third of the dish and both strains CM601 and the strains presenting resistance are deposited on the last third of the dish.

3) After 2 days at 30° C., bacteria are recovered in the crossing area and selected on the selective medium (Sz Azelate+Tet 20 µg/ml=hist−medium, Tet+) on which only the recombinants grow (= bacteria which have inserted the Tn4431 transposon).

4) The recombinant are replicated on dishes containing different metals (in gluconate 284 medium) and the mutants which emit light in the presence of specific metals are selected for further study.

The concentrations of the metal on the Petri dishes are the following:

284 gluconate+chromium 40 µg/ml 284 gluconate+nickel 2 mM 284 gluconate+cobalt 2 mM 284 gluconate+zinc 2 mM
284 gluconate+cadmium 0.8 mM
284 gluconate+lead 0.3 mM
284 gluconate+copper 0.8 mM A preferred cellular host is *Alcaligenes eutrophus* type are interesting for the following reasons:

- they present a high ability of specific resistance expression to a metal,
- these mechanisms are inducible (Siddigui et al., 1988, Inductible and constitutive expression of pMOL 28-encoded nickel resistance in *Alcaligenes eutrophus* N9A. J. Bacteriol. 170, 4188–4193; Nies et al., 1989, Plasmid-determined inductible efflux is responsible for resistance to cadmium, zinc, cobalt and nickel in *Alcaligenes eutrophus*. J. Bacteriol. 171, 896–900; Senfuss et al., 1989, Plasmid PMOL 28 encoded resistance to nickel is due to a specific efflux. FEMS Microbiol. Lett. 55, 295–298);
- it is a good recipient for exogenous genes in heterospecific conjugations (Lejeune et al., 1983, Chromosomal transfer and R-prime plasmid formation mediated by plasmid pULB113 (RP4::Mini-Mu) in *Alcaligenes eutrophus* CH34 and *Pseudomonas fluorescens* 6.2. J. Bacteriol. 155, 1015–1026).

The invention also relates to a process wherein the cellular host containing a promoter and a gene encoding the resistance to a metal is *Alcaligenes eutrophus* and the cellular host containing a transposon is *E. coli* containing the vector pUCD623, itself containing a transposon Tn4431 which is Tn21 transposon containing the tetracycline resistance and the lux operon of *Vibrio fischeri* without its own promoter,

- the selection of the obtained transconjugants is carried out on tetracycline plates,
- the transconjugants are replicated on media with different concentrations of metals,
- the detection of the light producing transconjugants is carried out.

The invention also relates to a process for preparing a cellular host emitting light in the presence of chromium, wherein the cellular host containing a promoter and a gene resistant to a metal is *Alcaligenes eutrophus* SV661 and the cellular host containing the transposon is *E. coli* strain CM601, which gives AE714, transferred into A5.3 to give AE859, which gives light expression in the presence of chromium.

The selection of the chromium biosensor is advantageously carried out (besides the marker and minimum medium) in the presence of zinc which enables to select the transconjugants which have not inserted said transposon in the zinc resistance gene.

The invention also relates to a process for preparing a cellular host emitting light in the presence of nickel, wherein the cellular host containing a promoter and a gene resistant to a metal is *Alcaligenes eutrophus* AE631 and the cellular host containing the transposon is *E. coli* strain CM601, which gives AE453, transferred into A5.3 to give AE891, which gives light expression in the presence of nickel.

The invention also relates to a process for preparing a cellular host emitting light in the presence of copper, wherein the cellular host containing a promoter and a gene resistant to a metal is *Alcaligenes eutrophus* DS185 and the cellular host containing the transposon is *E. coli* strain CM601, which gives AE866, which gives light expression in the presence of copper.

The invention also relates to a process for preparing a cellular host emitting light in the presence of copper, wherein the cellular host containing a promoter and a gene resistant to a metal is *Alcaligenes eutrophus* DS310, and the cellular host containing the transposon is *E. coli* strain CM601, which gives AE890, which gives light expression in the presence of copper and cannot grow on minimal plates containing lead.

The invention also relates to a process for preparing a cellular host emitting light in the presence of a biphenyl compound, wherein the cellular host containing a promoter and a gene encoding the catabolism of biphenyl compounds is *Alcaligenes eutrophus* A5 and the cellular host containing the transposon is *E. coli* strain CM601, which gives A5.23 or A5.24, which gives light expression in the presence of biphenyl compounds.

The invention also relates to *E. coli* liable to be transformed according to the process of the invention.

The invention also relates to *Alcaligenes eutrophus* liable to be transconjugated according to the process of the invention.

The invention also relates to a process for detecting, on a solid medium, a metal or a xenobiotic compound, preferably in a concentration range of about 1 to about 120 ppm, comprising:

- the use of a solid support, such as an agar disc containing an appropriate solid medium for a cellular host of the invention,
- the application, on said agar disc, of a cellular host of the invention contained in a liquid medium,
- placing a radiographic film under the above-mentioned agar disc,
- detecting the bioluminescence by comparison on the film of the blackening of the film.

The invention also relates to a process for detecting, in a liquid medium, a metal or a xenobiotic compound, preferably in a concentration range of about 1 to about 120 ppm, comprising:

- placing cellular hosts of the invention which have been lyophilyzed and immobilized on a solid support, into a liquid medium,
- introducing a sample of said liquid culture medium, containing cellular hosts of the invention, in a sample taken from a liquid medium, such as water, in which the presence of a metal or of a xenobiotic compound is to be detected,
- detecting the signal, for instance, the light generated by the presence of said metal or the presence of said xenobiotic compound, by detecting means such as a luminometer.

The invention also relates to a process for detecting in a liquid medium a metal or a xenobiotic compound, preferably in a concentration range of about 1 to about 120 ppm, comprising:

- introducing a cellular host of the invention contained in a liquid medium, into a sample taken from a liquid medium, such as water,
- detecting the signal, for instance, the light generated by the presence of said metal or the presence of said xenobiotic compound by detecting means such as a luminometer.

The invention also relates to a kit for detecting a metal or a xenobiotic compound in a concentration range as little as 0,1 ppm for metals and as little as 1 ppb for xenobiotics, comprising:

- a cellular host of the invention,
- detection means, for instance to detect the light generated by the presence of said metal or xenobiotic compound, such as a luminometer.

By way of example:
1) a preculture is obtained by inoculation of an isolated colony of a cellular host of the invention in a rich liquid medium such as 869, preferably containing 20 μg/ml of tetracycline, to select only the cellular hosts in which the transposon has been inserted;
2) the culture is diluted, for instance 20 times, in the liquid sample containing the metal or xenobiotic to be determined in a final volume of about 0.5 ml;
3) bioluminescence is measured, for instance with a luminometer.

COMMENTS ON THE FIGURES

FIG. 1 represents bioluminescence by zinc (in the form of $Zn^{2+}$) induced strain CM685 expressed in bioluminescence units (cpm) plotted against the time (in hours).

Strain CM685 was cultured overnight in liquid medium 869. Aliquots of 10 μl were applied on standardized agar discs with or without 1 mM zinc (see materials and methods) which were transferred into sterile vials of a scintillation counter. Bioluminescence was monitored automatically every hour.

The results represent average values of triplicate samples and the associated standard error of the mean (S.E.M.). The curve comprising the triangles correspond to samples containing 1 mM $Zn^{2+}$. The curve comprising the circles correspond to control samples.

FIG. 2 represents the signal/noise ratio plotted against time (in hours) for bioluminescence of zinc (in the form of $Zn^{2+}$) induced strain CM685 on agar discs.

Strain CM685 was cultured overnight in liquid medium 869. Aliquots of 10 μl were applied on standardized agar discs which contained 1 mM zinc. The measured bioluminescence signal was divided by the signal of parallel vials containing the same amount of bacteria growing on agar discs without zinc.

FIG. 3 represents the cobalt (in the form of $Co^{++}$) induced bioluminescence expressed in mV/versus the time (in hours) on solid agar.

Strain CM781 was cultured overnight in liquid medium 869. After 20 fold dilution, 10 μl aliquots were. evenly distributed over the surface of punched out mini agar discs containing increasing concentrations of $Co^{++}$.

Bioluminescence was monitored automatically every 30 min after transfer of the agar discs into the bottom of sterile luminometer tubes. The gain of the photomultiplier is stabilized automatically in this instrument, facilitating measurements over long periods.

The results are the average from 5 duplicate samples.

The curve comprising "+" correspond to samples containing no $Co^{++}$.

The curve comprising triangles correspond to samples containing 0.2 mM $Co^{++}$.

The curve comprising circles correspond to samples containing 0.5 mM $Co^{++}$.

The curve comprising "+" correspond to samples containing 1.0 mM $Co^{++}$.

FIG. 4 represents chromium (in the form of chromate) induced bioluminescence on agar (expressed in relative light units) containing minimal medium versus the amount of chromium added.

Strain AE859 was grown in minimal liquid medium 284+gluconate during 70 h. Aliquots of the undiluted culture were transferred on standardized agar discs as described in materials and methods.

The total light output during 3 days growth in the luminometer was calculated for each group and corrected for differences in growth, as measured by turbidimetry. The resulting relative light output is plotted against the chromium concentrations used.

FIG. 5 represents the signal/noise ratio of AE859 grown on agar 869 versus the amount of chromium (in the form of chromate) added (in mM).

Strain AE859 was grown during 23 h in liquid medium 869. Undiluted aliquots of 10 μl were transferred on standardized discs of agar containing growth medium 869. The signal/noise ratio is calculated as indicated in FIG. 2 except for the length of the growth in the luminometer which was 2 days. No light was produced after more than 20 hours. The results are corrected for small differences in growth.

FIG. 6 represents the bioluminescence (in mV)of AE866 versus the copper (in the form of $Cu^{2+}$) concentrations (in ppm).

Strain AE866 was grown during 16 h in liquid medium 869. Undiluted aliquots of 10 μl were transferred as described above. Each value represented the maximum mean value of 15 aliquots at different copper concentrations.

FIG. 7 represents bioluminescence (expressed in cpm) versus the time, of strains inducing light in the presence of chlorinated compounds.

Strain A5-24 was grown on agar discs containing minimal medium 284+gluconate during the time indicated. Small cristals of biphenyl or 4-chlorobiphenyl were placed at the bottom of the scintillation vial without direct contact with the agar discs. Transformer oil (askarel) (10 microliters) was also deposited next to the agar discs in such a way that only volatile components could reach the bacterial growth.

The curve with circles corresponds to control samples.

The curve with black triangles pointing downward corresponds to samples containing biphenyl.

The curve with black squares corresponds to samples containing 4-chlorobiphenyl.

The curve with black triangles pointing upward corresponds to samples containing transformer oil.

FIG. 8 represents an enhanced bioluminescence of strain A5.23 after preadaptation to biphenyl.

The curve containing black triangles pointing downward corresponds to the bioluminescence in the presence of biphenyl of strain A5.23 after preadaptation to biphenyl.

The curve containing circles corresponds to the bioluminescence in the absence of biphenyl of strain A5.23 after preadaptation to biphenyl.

Strain A5-23 grown during 3 days on minimal agar 284+gluconate in the presence of volatile biphenyl cristals, was harvested, resuspended in a small volume (50 μl) liquid medium 284+gluconate without inducer and transferred in 8 μl aliquots to fresh agar discs with or without biphenyl cristals. Bioluminescence measurements were started immediately thereafter.

FIG. 11 represents a DNA sequence identified by SEQ ID NO:1 (top strand) and by SEQ ID NO:2 (bottom strand) of the EcoRI-SalI fragment of aE23 of pMOL 149 (see FIG. 10), said DNA sequence enabling the induction of lux genes by zinc. The ORF are represented in darker characters.

Figure 1:
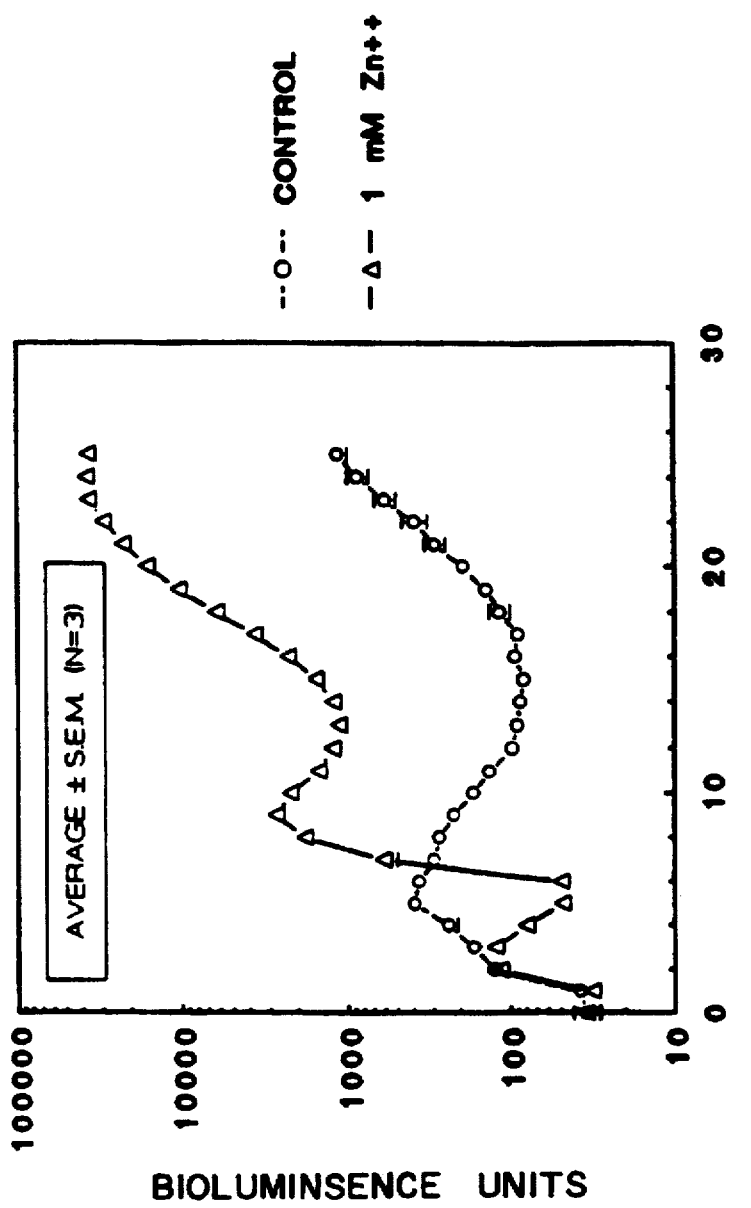

The metals have been used at the following concentrations:

■0.01 mM ▦0.1 mM ▨0.2 mM ☐0.4 mM

In other words:

the black pattern corresponds to a concentration of 0.01 mM of metal, the fine cross hatching pattern corresponds to a concentration of 0.1 mM of metal, the diagonal lines pattern corresponds to a concentration of 0.2 mM of metal, the coarse cross hatching pattern corresponds to a concentration of 0.4 mM of metal.

MATERIALS AND METHODS

In the following example, the cellular hosts emitting light in the presence of a metal or in the presence of a xenobiotic compound will be named "biosensors".

Bacterial strains and plasmids

The metal resistance genes, used for the gene fusions, are isolated from *Alcaligenes eutrophus* CH34 ("*Alcaligenes eutrophus* CH34 is a facultative chemilithotroph with plasmid-bound resistance to heavy metals" M. Mergeay et al. (1985), J. Bacteriol. 162: 328–334) or related strains (Diels L. et al., 1990, "DNA probe-mediated detection of resistant bacteria from soils highly polluted by heavy metals" Appl. Environ. Microbiol. 56:1485–1491). On the other hand, the biphenyl degrading genes come from another *Alcaligenes eutrophus* strain A5 (Shields M. S. et al., 1985, "Plasmid-mediated mineralization of 4-chlorobiphenyl", J. Bacteriol. 163:882–889).

Construction of New Fusions By in Vitro Cloning
a) Construction of a zinc biosensor:

A zinc biosensor was constructed by cloning in *E. coli* (S17/1). A SalI fragment (3.5 kb) from pMOL149 (hereafter described) (pBR325 with the czc fragment of pMOL30 from CH34 and its surrounding EcoRI fragment) was inserted in the promoter expressing vector pUCD615 (said vector being contained in a strain of *E. coli*, CM600 deposited at the C.N.C.M., Institut Pasteur, 28 rue du Docteur Roux, 75015 Paris, on Feb. 28, 1991, under n° I-1050). Plasmid pBR325 comprises a complete copy of pBR322 (ATCC No. 31344; U.S. Pat. No. 4,342,832 and No. 4,366,246) (I-A-iv-I) opened at the EcoRI site and a 1.2 kb HaeII fragment containing the cml gene. Plasmid pBR325 has been certified by the NIH Recombinant DNA Advisory Committee as an EK2 vector (Recombinant DNA Technical Bulletin, NIH5 (1982)). The nucleotide sequences of pBR325 is known. The digestion with SalI in the multiple cloning site of pUCD615 and in pMOL149 are done according to Maniatis et al. (1982), p. 104–105. After the dephosphorylation (Maniatis et al., 1982, p. 133–134) of pUCD615, the ligation (Maniatis et al., 1982, p. 125–126) with the SalI fragments was carried out. Selection was done on ampicillin plates with 0.5 mM ZnCl$_2$. Light producing colonies were selected with autoradiography and with Polaroid photography.

This biosensor is hereafter designated by CM685.

The detailed protocol is given hereafter.

1. Curing of CH34 and creation of AE128:

An erlenmeyer flask (50 ml) containing 5 ml of 284-gluconate medium with mitomycin C (4 µg/ml) was shaken at 30° C. during 5 days. Cells from the flask were harvested, washed, diluted and spread on agar plates containing 284-gluconate with 2 mM NiCl$_2$. Plasmid-deficient mutants occurred at a frequency of $10^{-3}$ to $10^{-5}$ per mitomycin C treated cell. Ni sensitive cells contained only pMOL30 and this was evaluated by agarose (0.8%) gel electrophoresis. This resulting strain was registered as AE128.

2. Isolation of pMOL30 from AE128:

An overnight culture of AE128 in medium M3 (Nutrient Broth (Difco) 8 g/l) (30 ml) was centrifuged during 10 minutes at 4000 rpm in 6 tubes of 5 ml. Each pellet was suspended in 1 ml E buffer (0.04M Tris-acetate pH 7.9; 0.002M EDTA). Afterwards, 2 ml lysis buffer (3% SDS; 0.05M Tris-OH pH 12.55) was added and incubated is glasstubes at 65° C. during 60 minutes.

Afterwards, 400 µl 5M NaCl and 6 ml phenol/CHCl$_3$ were added and mixed followed by a centrifugation of 10 minutes. Then the tubes were incubated at 4° C. during 1 hour. The bottom phase was eliminated and the top phase centrifuged again (10 minutes).

The top phase was casted in a siliconised glass tube. 30 µl 10% acetic acid was added and 6 ml diethyl ether and agitated. After centrifugation and removal of the ether layer, the tubes were incubated at 65° C. during 10 minutes to remove the traces of ether. The DNA was precipitated with 50 µl 5 mM NaCl and 2 ml ethanol. After a 2 hour incubation at −15° C. the tubes were centrifuged during 15 minutes. All the six pellets were dissolved in 2.0 ml water, 200 µl 5 M NaCl and 4.4 ml ethanol added. After a 2 hour incubation at −15° C. the tubes were centrifuged and the pellet dried and dissolved in 200 µl H$_2$O.

3. Digestion of pMOL30 with EcoRI:

To 20 µl of pMOL30 2.5 µl of 10×EcoRI buffer, 4 µl RNase solution and 1 µl EcoRI (50 U/µl) were added. After incubation at 37° C. during 2 hours, the DNA was treated with a phenol extraction and precipitated with ethanol. The DNA pellet was dissolved in 50 µl TE buffer.

Figure 9:
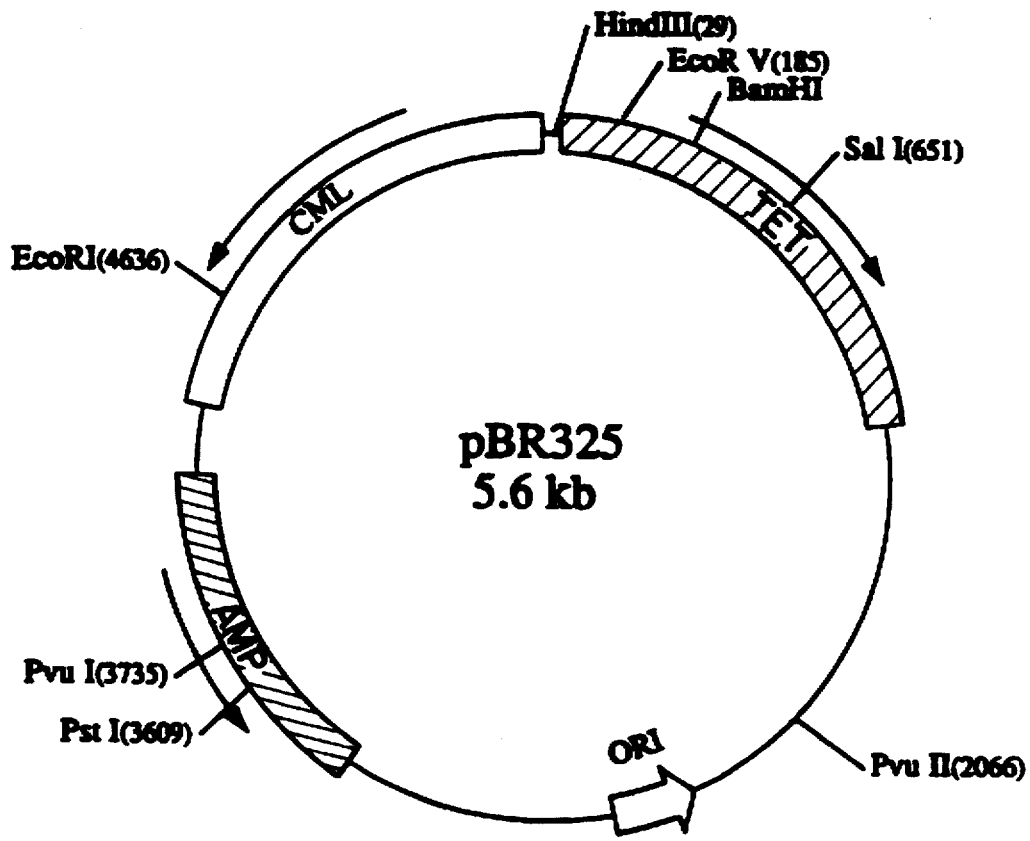
FIG. 9 represents the cartography of plasmid pBR325 (5.6 kb).

4. Digestion of pBR325 with EcoRI:

To 20 µl of pBR325 (cf. FIG. 9) (2 µg/10 µl) 2.5 µl of 10×EcoRI buffer, 4 µl RNase solution and 0.5 µl EcoRI (50 U/µl) were added. After incubation at 37° C. during 2 hours, the DNA was treated with a phenol extraction and precipitated with EtOH.

5. Dephosphorylation of EcoRI digests of pBR325:

To a pellet 35 µl 10 mM Tris-HCl pH 8 buffer and 4 µl of CIP buffer (0.5M Tris-HCl pH 9.0; 10 mM MgCl$_2$; 1 mM ZbCl$_2$; 10 mM spermidine+2 µl CIP (0.5 U) were added and incubated at 37° C. during 30 minutes. Afterwards, again 2 µl C/P was added for a second incubation of 30 minutes.

50 µl water and 10 µl 10×STE (100 mM Tris-HCl pH 8; 1 mM NaCl; 10 mM EDTA and 1 µl 20% SDS were added and incubated at 68° C. during 15 minutes. One phenol/CHCl$_3$ and one CHCl$_3$ extraction were done followed by an ethanol precipitation with 10 µl 5M NaCl and 330 µl EtOH (precipitation at −70° C. during 15 minutes).

6. Ligation of pBR325 EcoRI with EcoRI digests of pMOL30:

To the pellet of (5) 40 µl H$_2$O and 5 µl ligation buffer (0.5 m Tris pH 7,4; 0.1 m MgCl$_2$; 0.1M dithiotreitol; 10 mM spermidine; 10 mM ATP; 1 mg/ml BSA and 12 µl of (3) were added and ligation was done with 4 µl ligase (10 to 20 U).

An overnight incubation of this ligation mixture was done at 12° C. Afterwards, 50 μl TE buffer (10 mM Tris-HCl pH 7.4; 1 mM EDTA) was added and after a phenol/CHCl$_3$ and CHCl$_3$ extraction, the DNA was precipitated with 10 μl 5M NaCl and 330 μl EtOH.

7. Transformation of HB101:

Transformation of E. coli HB101 was done according to the CaCl$_2$ method of Maniatis et al. Selection was done for Tet$^R$, Amp$^R$ and Cm$^S$ clones.

Figure 10:
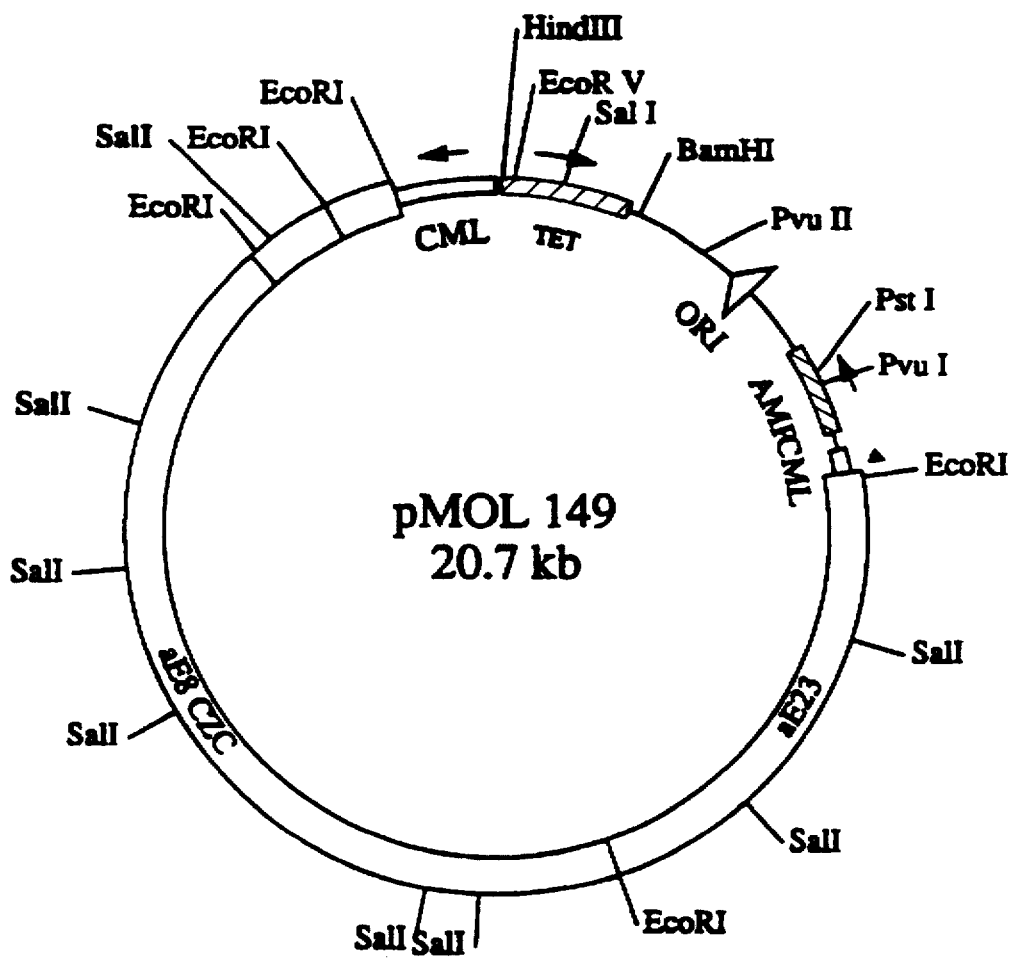
FIG. 10 represents the cartography of plasmid pMOL149 (20.7 kb).

Clone CM485 which contained pMOL149 (cf. FIG. 10) being pBR325 with aE8, aE23, aE38 and aE39 of pMOL30. pMOL149 was isolated according to Birnboin and Dolly (Nucl. Acid. Res. 7:1513).

8. SalI digestion of pMOL149:

pMOL149 was digested in the same way as explained in (3) 1 μl SalI enzyme (50 U) and 2.5 μl SalI digestion buffer was used.

9. SalI digestion of pUCD615:

pUCD615 (isolated from E. coli CM600 deposited at the C.N.C.M., Institut Pasteur, 28 rue du Docteur Roux, 75015 Paris, on Feb. 28, 1991, under n° I-1050 according to Birnboin above-mentioned) was digested in the same way as pMOL149 (8).

10. Dephosphorylation of pUCD615 SalI:

The dephosphorylation of pUCD615 SalI was done in the same way as explained in (5).

11. Ligation of pMOL149 SalI with pUCD615 SalI:

The ligation between pMOL149 SalI and pUCD615 SalI was done according to (6).

12. Transformation of the ligate in S17/1:

The ligate was transformed into S17/1 according to Maniatis et al. (p250). Selection was done on Amp$^R$ transformants.

13. Selection of phenotype lux$^+$ with 0.5 mM Zn:

Amp$^R$ transformants were replicated on Petri dishes with LB broth+50 μg Amp with addition of 0, 0.1, 0.2, 0.5, 1.0 mM ZnCl$_2$. These dishes were put on X-ray films during incubation in cardboard boxes. Colonies giving more and more light at increasing Zn concentrations were selected and purified and their phenotype further analysed in a luminometer experiment.

b) Construction of a cobalt biosensor:

A cobalt biosensor was created in the same way as the above described zinc biosensor by inserting an EcoRI-PstI fragment (<0.1 kb) from pMOL149 in pUCD615. The PstI site was made blunt end (Maniatis et al. (1982), p. 394–395) and afterwards a phosphorylated EcoRI linker was attached (Maniatis et al. (1982), p.396–397) to that site. The linker was digested with EcoRI (Maniatis et al. (1982), p. 104–105) and the fragment was ligated (Maniatis et al. (1982), p.125–126) to pUCD615. Selection was done on ampicillin plates with 0.5 mM CoCl$_2$. Light producing colonies were selected with autoradiography.

This biosensor is hereafter designated by CM781.

Construction of New Fusions By In Vivo Cloning

Different Alcaligenes strains were conjugated with the E. coli strain CM601 (deposited at the C.N.C.M., Institut Pasteur, 28 rue du Dr Roux, 75015 Paris, on Feb. 28, 1991, under n° I-1051) bearing the suicide vector pUCD623 with the lux transposon Tn4431 (without its own promoter). After conjugation, transconjugants were selected on tetracycline plates. Afterwards transconjugants were replicated on media with different concentrations of heavy metals. In this way different biosensors could be constructed.

a) Construction of a chromium biosensor:

A chromium biosensor could be obtained by conjugation of the chromium resistant Alcaligenes eutrophus SV661 strain (deposited at the C.N.C.M., Institut Pasteur, 28 rue du Dr Roux, 75015 Paris, on Feb. 28, 1991, under n° I-1046) (Diels L. et al., 1990, "DNA probe-mediated detection of resistant bacteria from soils highly polluted by heavy metals" Appl. Environ. Microbiol. 56:1485–1491) with CM601. Selection was done on mineral medium (Schlegel H. G. et al., 1961, "Ein submersverfahren zur kultur wasserstoffoxidierender bakterien: wachstums physiologische untersuchungen" Arch. Mikrobiol. 38:209–222) with 20 mg/l tetracycline and 2 mM zinc. The obtained transconjugants were transferred on mineral plates with 1 mM CrO$_4^-$. Light emitting colonies were selected by autoradiography.

This biosensor is hereafter designated by AE714.

The construction of the invention contained in AE714 was transferred in A5.3 to give a stable strain AE859.

b) Construction of a nickel biosensor:

A nickel biosensor was obtained after mating between AE453 and CM601 (AE453 has been deposited at the C.N.C.M., Institut Pasteur, 28 rue du Dr Roux, 75015 Paris, on Feb. 28, 1991, under n° I-1049). After selection on tetracycline the transconjugants were selected on mineral medium with 0.5 mMNiCl$_2$.

This biosensor is hereafter designated by AE631.

The construction of the invention contained in AE631 was transferred in A5.3 to give a stable strain AE891.

c) Construction of a copper biosensor:

Copper biosensor were obtained after mating between DS185 or DS310 bearing each pMOL90, 85 and 80 (Diels L. et al., 1990, "DNA probe-mediated detection of resistant bacteria from soils highly polluted by heavy metals" Appl. Environ. Microbiol. 56:1485–1491) and CM601.

DS185 has been deposited at the C.N.C.M., Institut Pasteur, 28 rue du Dr Roux, 75015 Paris, on Feb. 28, 1991, under n° I-1048.

DS310 was obtained from DS185 as follows:

A 5 ml culture of DS185 in 284 gluconate medium with SDS (0.01%) was shaken in an erlenmeyer flask (50 ml) at 30° C. during 4 days. Cells from the flask were harvested, washed, diluted and spread on agar plates containing 284 gluconate with 2 mM Zn. Plasmid analysis was performed according to Kado C. I. et al. (1981), "Rapid procedure for detection and isolation of large and small plasmids" J. Bacteriol. 145:1365–1373. DS310 was obtained by this way and had lost the pMOL80 plasmid (4 kb).

From the mating between DS185 and CM601, 200 colonies were tested and from the mating between DS310 and CM601, 200 colonies were also tested.

The selection was realized as described above on minimal plates with 0.8 mM copper as inductive agent and tetracycline.

These biosensors obtained respectively with DS185 and DS310 are hereafter designated by AE866 and AE890.

d) Construction of biphenyl biosensor:

Two biphenyl biosensors were obtained after mating between A5 and CM601. After selection on tetracycline the transconjugants were screened for light induction on minimal plates with biphenyl as inductive agent.

These biosensors are hereafter designated by A5.23 and A5.24.

Conjugation With A5.3

The in vivo made constructions in Alcaligenes eutrophus var. metallotolerane contained rather unstable Tn4431 insertions. Therefore the plasmids were transferred to A5.3. The strain A5.3 is a rifampicin mutant of the biphenyl degrading strain A5 (A5 has been deposited at the C.N.C.M., Institut Pasteur, 28 rue du Dr Roux, 75015 Paris, on Feb. 28, 1991, under n° I-1047). This mutant is obtained by spreading A5 on agar plates containing Luria Broth medium with 100 μg/ml rifampicin. Resistant colonies are selected. After conjugation, selection was done on minimal plates containing tetracycline, rifampicin. The obtained transconjugants were tested for their resistance to chromium (biosensor designated by AE859) or nickel (biosensor designated by AE891) respectively and for their light expression on these metals.

Measurement of Bioluminescence

Luminescence was quantitated with a scintillation counter (Packard Tri-Carb model 2425) set in the chemiluminescence detection mode or with a luminometer (Bio-Orbit model 1251). In the former instrument, the bioluminescent activity was reported in cpm whereas in the latter instrument, bioluminescence is expressed in mV.

Induction experiments were performed on cultures of mutant strains in sterile vials cycled continuously for the duration of the experiment in the bioluminescence counter.

To measure optical density from liquid cultures, samples were removed from larger parallel cultures.

To measure bacterial growth at the end of cultures grown on calibrated agar discs (9 mm ø, 3.5 mm thick), the bacteria were dislodged from the agar by vigorous shaking during 1 h in 2 ml $MgSO_4$ 10 mM in closed tubes.

The turbidity of the supernatant was read at 630 nm using a Perkin Elmer spectrophotometer model lambda 3.

Experiments with fusion strains were performed at or below 30° C. since luciferase is inactivated at higher temperatures. Luminescence, where reported in relative light units, is normalized through division by the measured turbidity of the cultures.

Semi-quantitative comparative measurement of bioluminescence by several strains on different media was performed as follows:

Petri-dishes containing the appropriate solid medium were calibrated by weight after 30 minutes drying at 30° C. The net weight of the agar was chosen so as to obtain an average thickness of the agar of 3.5±0.1 mm in the central portion of the plate.

Using a sterile cork-bore with an internal diameter of 9 mm, agar discs were punched out from the central portion of the agar and transferred with a small spatula to sterile, empty Petri-dishes.

A liquid preculture, grown during the appropriate time was applied, diluted or not, in 10 microliter aliquots on each 9 mm agar minidisc. Care was taken during pipetting to disperse the culture evenly over the whole surface of the minidiscs. Triplicate (or more) samples are used for each group.

The Petri dishes are fixed in dark plastic (4 mm thick) plates, provided with 6 circular cutouts wherein the minidishes fit snugly.

A radiographic film (Kodak Ortho G) is placed under the Petri-dishes which are exposed in triple cardboard boxes during several hours or days, at the optimal temperature.

At the end of the exposure, the film is developed and the intensity of bioluminescence is judged by comparison of the blackening of the film under the minidiscs. If desired, corrections for differences in overall growth can be made by turbidimetry of the resuspended bacteria (v.s.).

This method gives a cumulative result of total light output during a given period but does not allow easily to follow the time-dependent light emission which is better quantitated using repeated measurements in a programmable luminometer. When more quantitative results over a given time segment were desired for bacteria, grown on solid agar, calibrated agar minidiscs were transferred to vials, appropriate for the bioluminescence counter of choice and measurements were performed at regular intervals on triplicate samples in sterile conditions.

Results

A. Light-Emitting Bacteria, Inducible By Heavy Metals

1) CM685: zinc biosensor

Different SalI fragments could be inserted in pUCD615. One of them containing plasmid pLD13 produced light on zinc plates. Another strain, bearing plasmid pLD10 produced also light on zinc plates but seemed to be extremely sensitive to zinc ions. Plasmid pLD13 contains a 3.5 kb SalI fragment overlapping the left site of the czc operon of pMOL30 from CH34 (ATCC 43123).

The bioluminescence, induced by 1 mM $zinc^{++}$ in solid growth medium is depicted in FIG. 1. During the first 7 hours, the toxicity of 1 mM $zinc^{++}$ is sufficiently high in this non-resistant E. coli strain to retard growth and decrease the light output in comparison with the control group.

After the induction period of about 8 h, the light output increases dramatically and reaches a level, at least 10 times higher than that of the control group.

Figure 2:
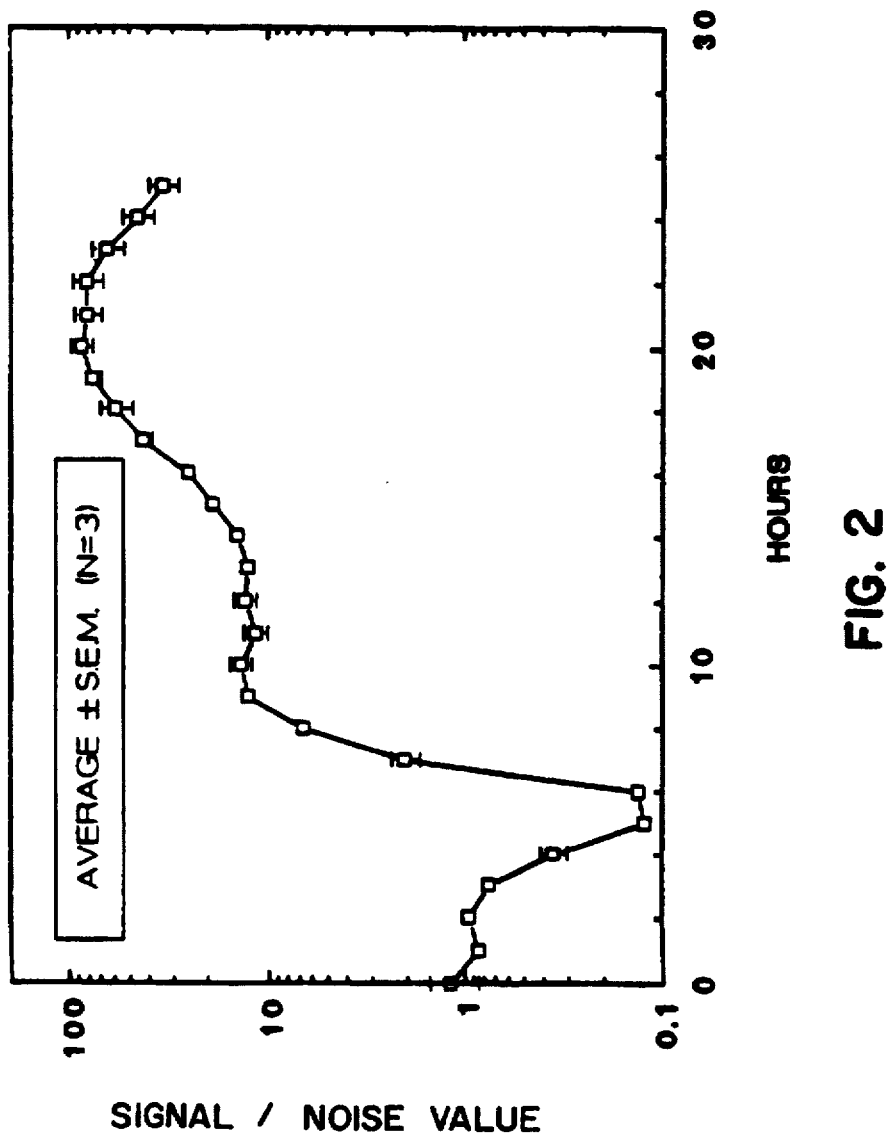

This enhanced bioluminescence is not due to better growth of bacteria on the zinc-containing agar because earlier experiments showed the contrary (data not shown). If the bioluminescence of the control group without zinc is taken as noise, a signal/noise ratio can be determined for each time period during 25 h of measurement. From FIG. 2, it follows that this ratio is very time-dependent in a complex way. The highest signal/noise ratio (86) is obtained after 21 hours.

When tested in liquid medium, this strain demonstrates only a marginally increased luminescence (+21% n=12) in the presence of 0.5 mM zinc during 24 hours at 30° C. with intermittent agitation in the luminometer.

The zinc promoter is characterized by the fact that it comprises a fragment of at least 20 contiguous base pairs of the DNA represented on FIG. 11, said fragment enabling the induction of lux genes by zinc.

2) CM781: cobalt biosensor:

From the several clones, obtained after EcoRI-PstI fragment insertion, one clone, emitting light on cobalt plates, could be obtained. The introduced EcoRI-PstI fragment is a very small one (<0.1 kb) and could until now not be identified in a clear way.

Figure 3:
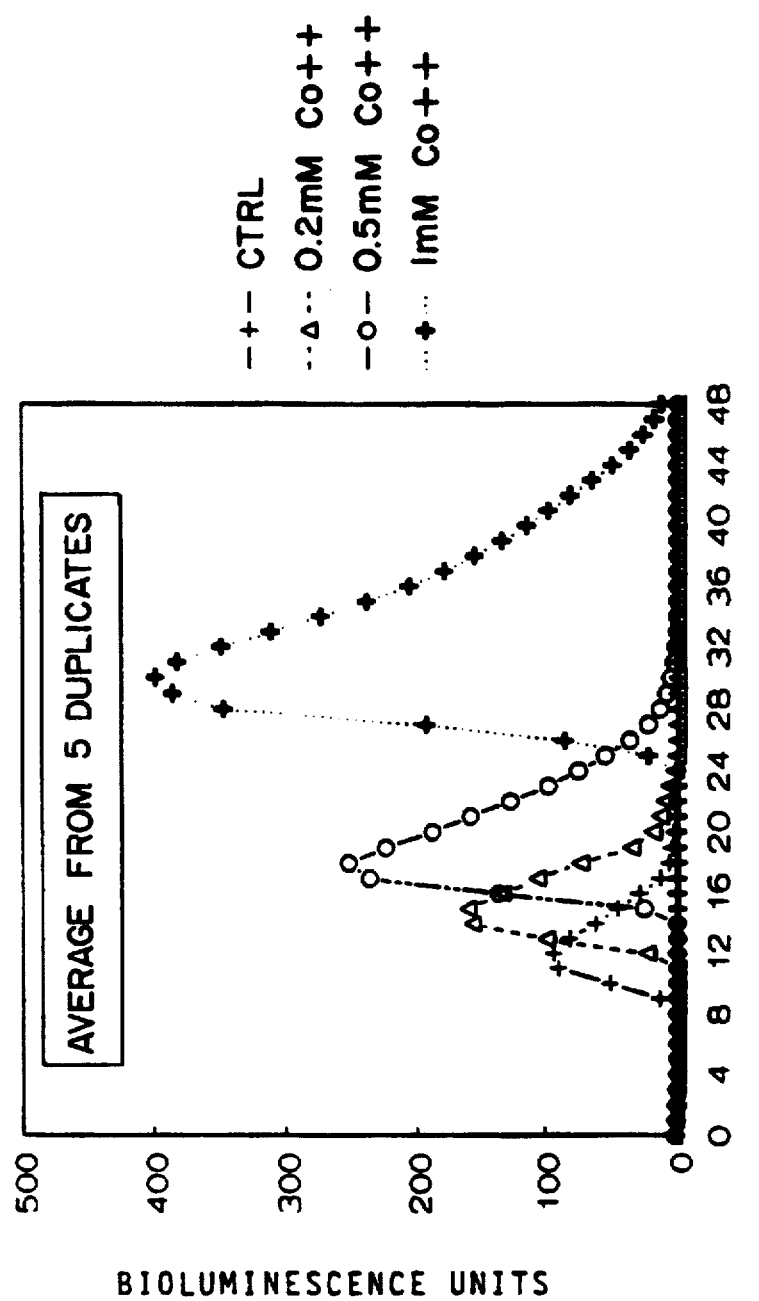

Cobalt being more toxic than zinc, different concentrations of this heavy metal were tested in solid nutrient agar. Increased $Co^{++}$ concentrations give rise to increased overall light output over a period of 48 hours. From FIG. 3 it is also obvious that the maximal bioluminescence is reached later when the $Co^{++}$ concentration increases.

In this strain, bioluminescence in liquid cultures decreases during a 24 h measuring period in the presence of increasing $Co^{++}$ concentrations (data not shown). However, recent experiments indicate that growth in the luminometer-vials is very slow and after 35 hours at 28.0° C. with intermittent agitation every 10 minutes, a considerable increase in bioluminescence is observed in the controls.

3) AE714: chromium biosensor:

The conjugation between SV661 and CM601 resulted among others in a $Ni^-$, $Cr^+$ AE714 mutant obtained by introduction of Tn4431 in pMOL28.661. The transposon Tn4431 was not very stable in *Alcaligenes eutrophus* var. *metallotolerans* and for that reason the plasmid pMOL28.661::Tn4431 was transferred to strain A5.3, a rifampicin resistant biphenyl degrading strain. This resulted in strain AE859 with a stable light expression on chromium ions.

In this strain also, the growth of the bacteria on the chromium containing agar was markedly inferior to that of the controls, as judged visually. At higher chromium concentrations, growth is very poor and light production faint (date not shown).

Figure 4:
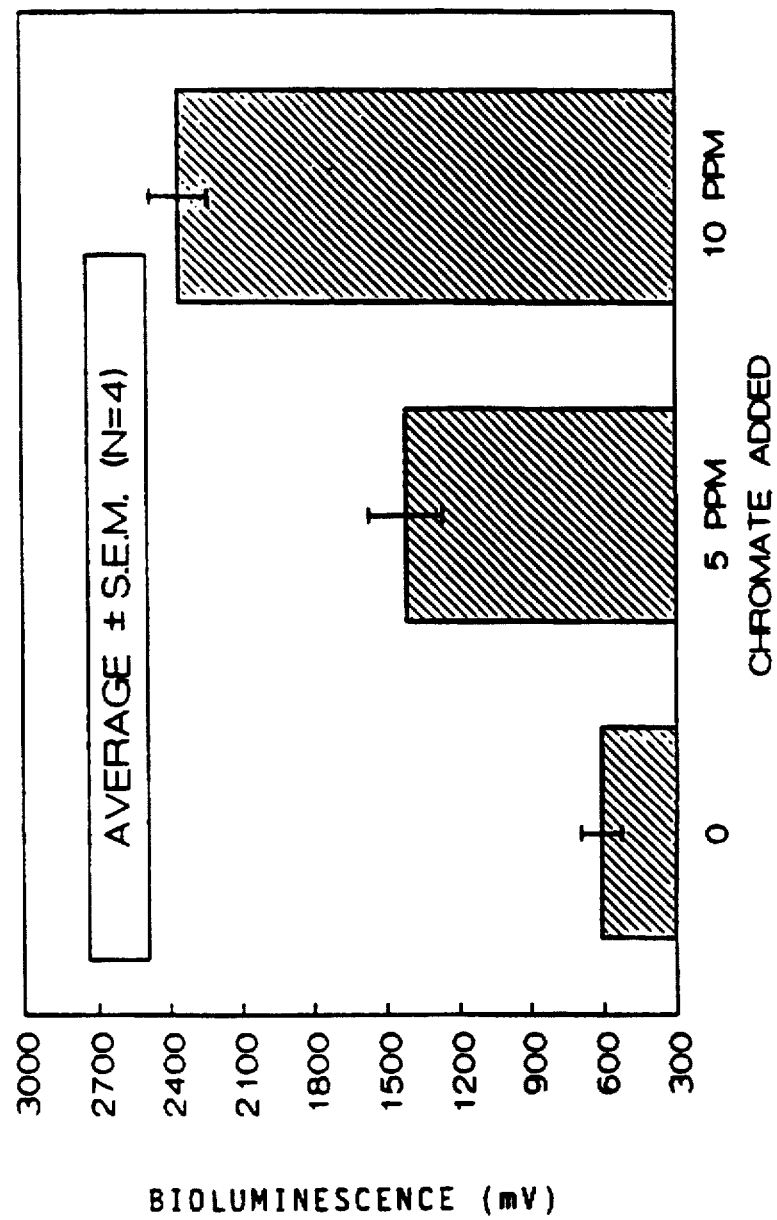

4) AE859: chromium biosensor:

This construct is more stable than strain AE714. When grown on minimal medium 284 glu during 3 days, the presence of chromium ions produces a linear increase in light output until 0.2 mM (FIG. 4).

Figure 5:
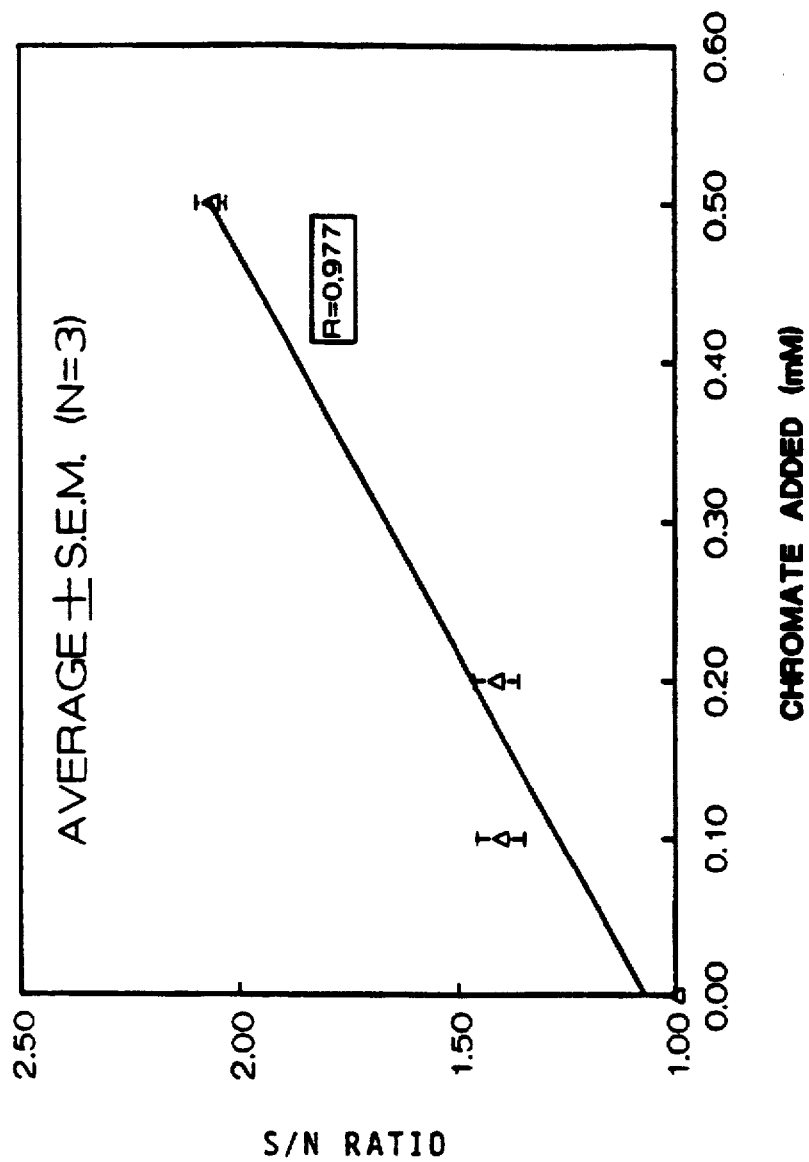

Growth and light production are faster when this strain is grown on agar containing a rich nutrient broth 869 but the signal/noise ratio reaches only a value of 2.06±0.03 at the highest chromium concentration tested (0.5 mM)(FIG. 5). This is due to the high background bioluminescence of the control group where the lux genes are not completely "silent" in the absence of added chromium. One possibility to explain this background is the presence of cryptic promoter sequences, unrelated to the heavy metal inducible promoter present in this mutant.

5) AE891: nickel biosensor:

The resulting strain from the conjugation of AE453 with CM601 was AE631 containing an insertion of Tn4431 in the ZinB gene resulting in a Zin⁻ strain. Also this strain was unstable and therefore pMOL55::Tn4431 was again transferred to A5.3 resulting in AE891 presenting a stable light emitting construction on nickel plates.

In the presence of at least 0.5 mM $Ni^{++}$ in minimal nutrient agar (284 glu) an increased bioluminescence is observed after 2 days of growth. This increase is still manifest at 1 and 2 mM $Ni^{++}$ where toxicity becomes limiting for adequate growth. The maximal signal/noise ratio (8,2±0.5) was reached in the presence of 1 mM $Ni^{++}$. The induction period for increased luminescence is at least 10 h at 30° C. in the presence of 0.5 mM $Ni^{++}$. At higher $Ni^{++}$ concentrations the induction period increases considerably.

Figure 6:
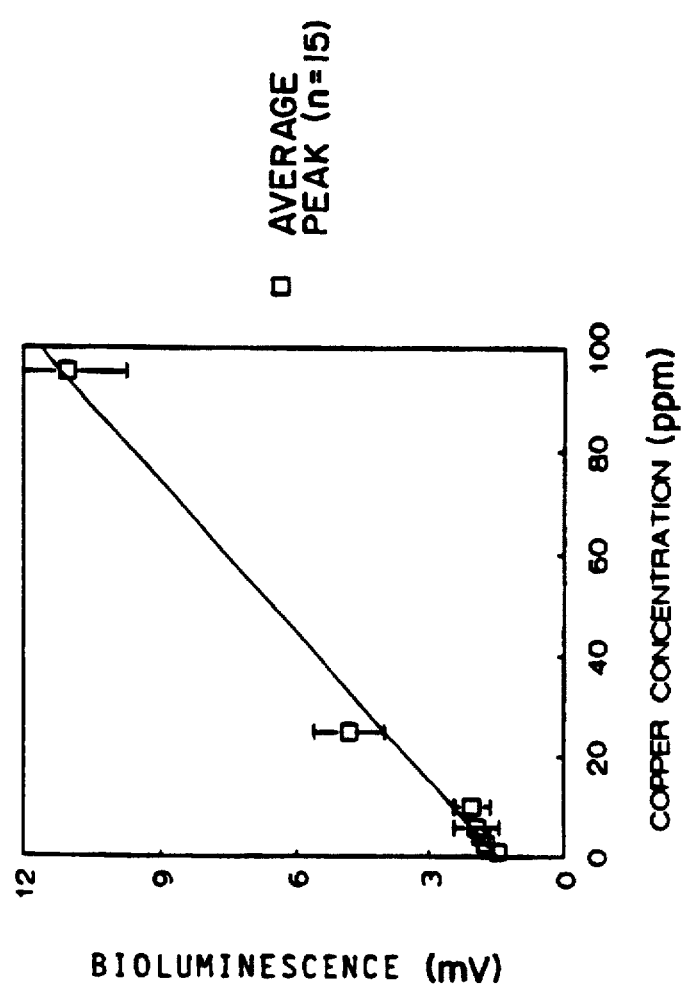

6) AE866 and AE890: copper biosensors:

The conjugation DS185 with CM601 gave AE866 by insertion of Tn4431 in pMOL85. The insertion of Tn4431 is located on pMOL85. The transconjugant AE890 results from the conjugation between DS185 and CM601. AE890 is sensitive for lead. A linear light response was observed for AE866 between 1 and 100 ppm on solid agar containing a rich nutrient broth 869 (FIG. 6). The light emission peak is obtained 9 to 10 h after induction and the detection limit with a signal/noise ratio of 2 was about 10 ppm copper. Above 100 ppm, light response was not more linear because of the toxicity of copper on the bacterial growth.

7) AE984: copper biosensor:

The strain AE984 is a derivative of strain AE866 which has lost spontaneously pMOL85 and which contains an insertion of Tn4431 in pMOL90 (pMOL90::Tn4431).

Figure 12:
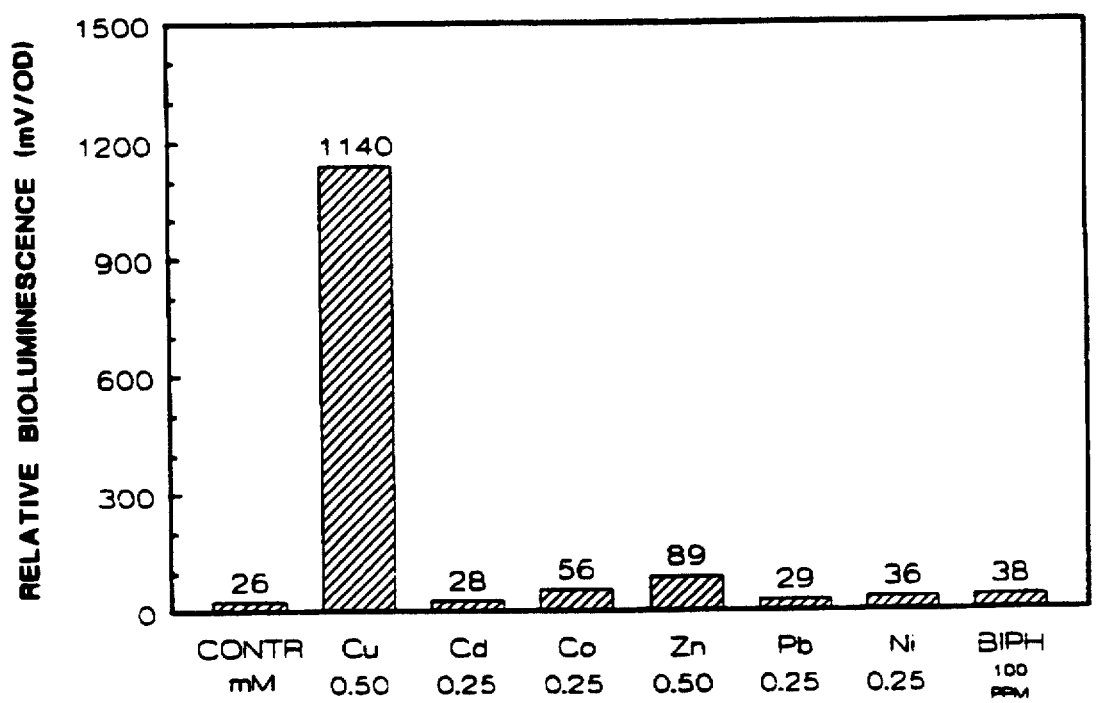
FIG. 12 represents the specificity of a copper biosensor (AE984 in medium 869 containing tetracycline [Tc]) compared to Cu, Cd, Co, Zn, Pb, Ni and biphenyl. Total bioluminescence after 24 h is expressed in mV.

FIG. 12 represents the specificity of AE984 with respect to copper. The background noise is obtained with the control sample. The specificity has been determined in the following conditions:

The strain AE984 was grown overnight at 30° C. The next day, dilutions were made with an optical density of 0.1.

Every test was done 3 times. Metal solutions were added to different tubes, to obtain final concentrations of:

control
0.5 mM Cu
0.25 mM Cd
0.25 mM Co
0.5 mM Zn
0.25 mM Pb
0.25 mM Ni
100 ppm Biphenyl.

Measurements were done in a Luminometer with 49 cycles every 30 minutes. Light is expressed in mV and the highest obtained values are presented.

When the tubes tested contain one of the following elements: Cd, Co, Zn, Pb, Ni or chlorinated biphenyl, no significant bioluminescence is observed.

7bis) AE984: copper biosensor:

In a second experiment strain AE984 was grown overnight at 30° C. The next day, dilutions were made to an optical density of 0.1.

Metal solutions were added to different tubes, to obtain final concentrations of 0.01; 0.1; 0.2 and 0.4 mM of the following metals:

control,
Cu,
Cd,
Zn,
Ni,
Co,
Cr,
Mn,
Ag,
Hg,
Tl.

Measurements were done in a Lumac luminometer after 18 hours of incubation at 21° C. Light was expressed in Relative Light Units (R.L.U.).

Figure 13:
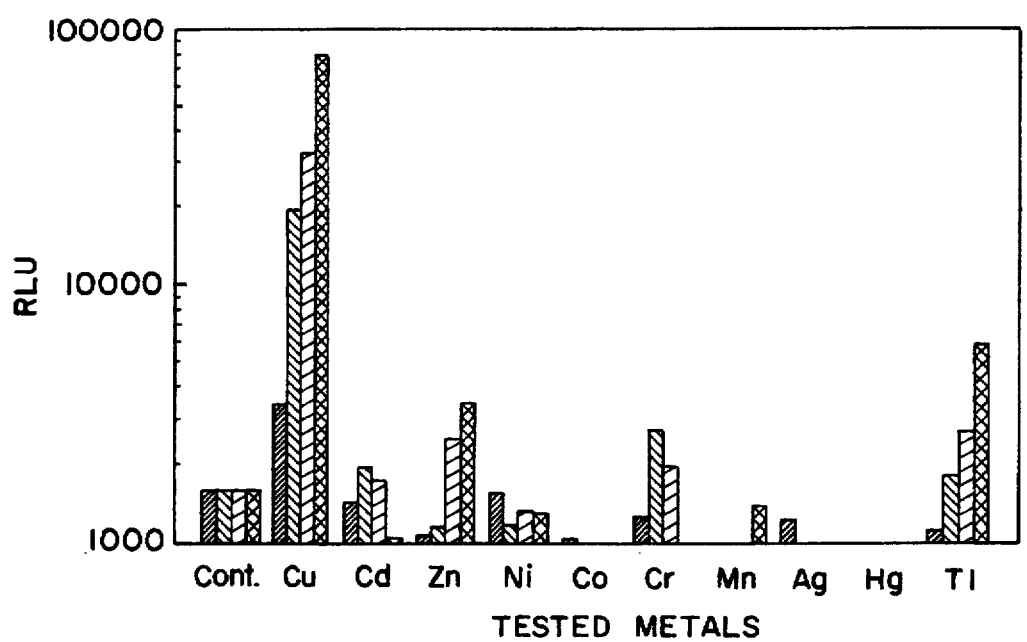
FIG. 13 represents the specificity of the same copper biosensor as in FIG. 12, compared to Cu, Cd, Zn, Ni, Co, Cr, Mn, Ag, Hg and Tl (at different concentrations). Bioluminescence is measured during 10 seconds and expressed in relative light units (RLU).

The results of these experiments are represented on FIG. 13.

8) Construction of thallium biosensors: AE1053, AE1060, AE1101:

A Tl sensor was constructed by conjugation between *E. coli* CM601 and *A. eutrophus* AE126.

The strain AE126 can be obtained by curing of CH34 with mitomycine C (5 µg/ml, 2 days incubation) and contains only plasmid pMOL28. This strain is sensitive to Zn (tested with $ZnCl_2$) and resistant with respect to Ni (tested with $NiCl_2$).

After conjugation, selection of transconjugants was done on minimal medium plates with gluconate as carbon source and with 20 µg/ml of tetracycline to select AE126 strains bearing the transposon. Afterwards, the transconjugants were tested on rich media (nutrient broth) with or without Tl and incubated with an autoradiography film on top of the Petri dishes. Strains inducing light in the presence of Tl were selected. The best strains were named AE1053, AE1060 and they were highly specific for Tl. No light induction was obtained by Co, Cs, or Cd. A very small induction could be obtained by Ni and Hg. Light was induced by insoluble (e.g. $Tl_2S$) and soluble (e.g. $TlNO_3$) compounds.

The light transposon Tn4431 was inserted in *A. eutrophus* chromosome as could be shown by hybridization of the transposon with *A. eutrophus* chromosome and plasmid DNA.

Strain AE1053 was afterwards conjugated with A5.3 (a rifampycin resistant A5 strain) and selection was done on minimal plates with rifampycin (100 μg/ml) and tetracycline (20 μg/ml). The resulting strain was AE1101 and displayed also light in function of increasing Tl concentrations.

Light was induced in the three strains AE1053, AE1060 and AE1101 by Tl concentrations between 0.005 mM and 0.02 mM for $Tl_2S$, and between 0.01 mM and 0.04 mM for $TlNO_3$.

B. Light emitting bacteria, inducible by chlorinated chemicals

A5-23 and A5-24: chlorinated biphenyl biosensors:

Two colonies specifically emitting light on biphenyl were obtained.

These strains A5-23 and A5-24 still kept the feature to use biphenyl as carbon source.

Figure 7:
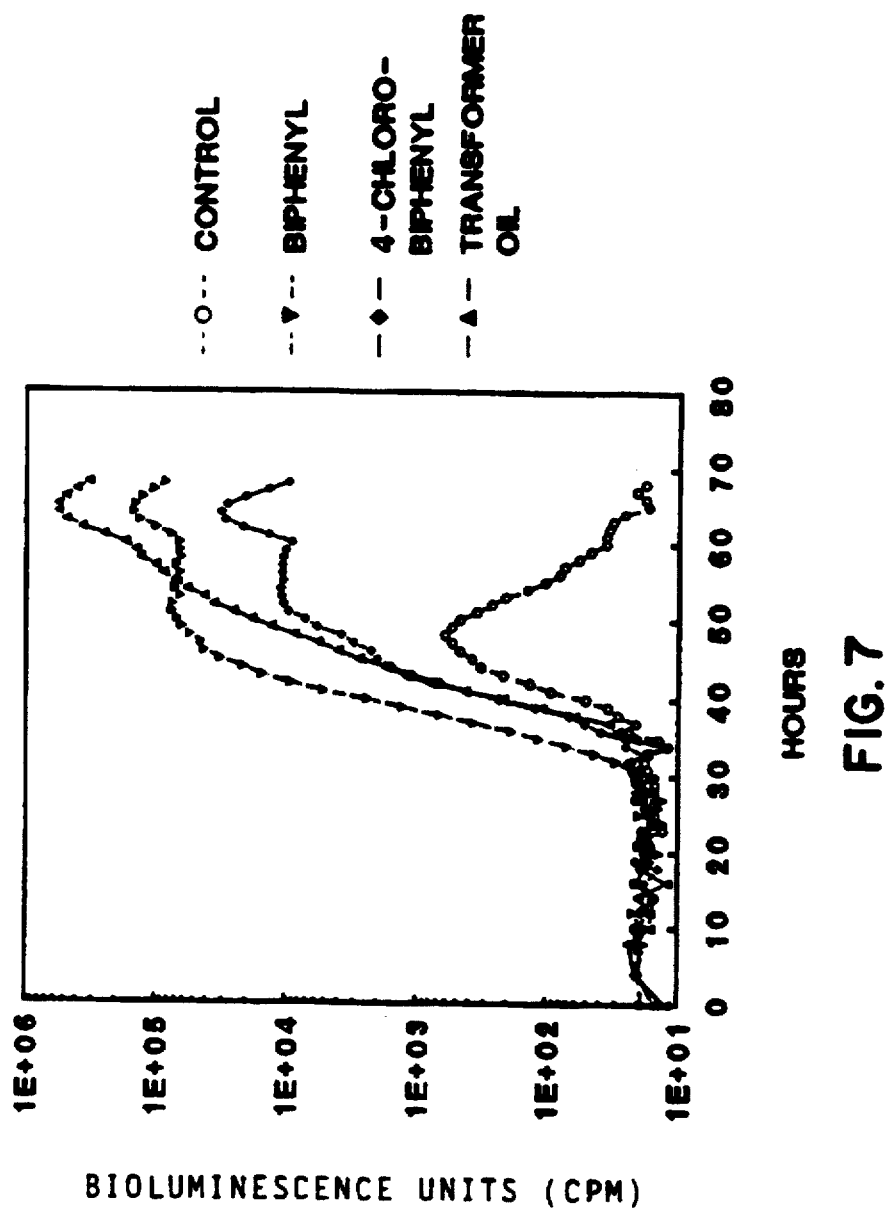

In the presence of biphenyl, some related aromatic compounds and transformer-oil (askarel: marketed by the Company ACEC, Belgium) these strains elicit a strongly enhanced bioluminescence (FIG. 7).

The time-lag before bioluminescence increases can be shortened drastically in these strains by prior exposure of the bacteria to the compounds of interest (pre-adaptation, i.e. pre-induction of certain genes), probably because pre-adaptation (with the specific metal or xenobiotic to be further detected) provokes the synthesis of certain specific gene products and is responsible for the beginning of degradation mechanisms or of resistance mechanisms.

Figure 8:
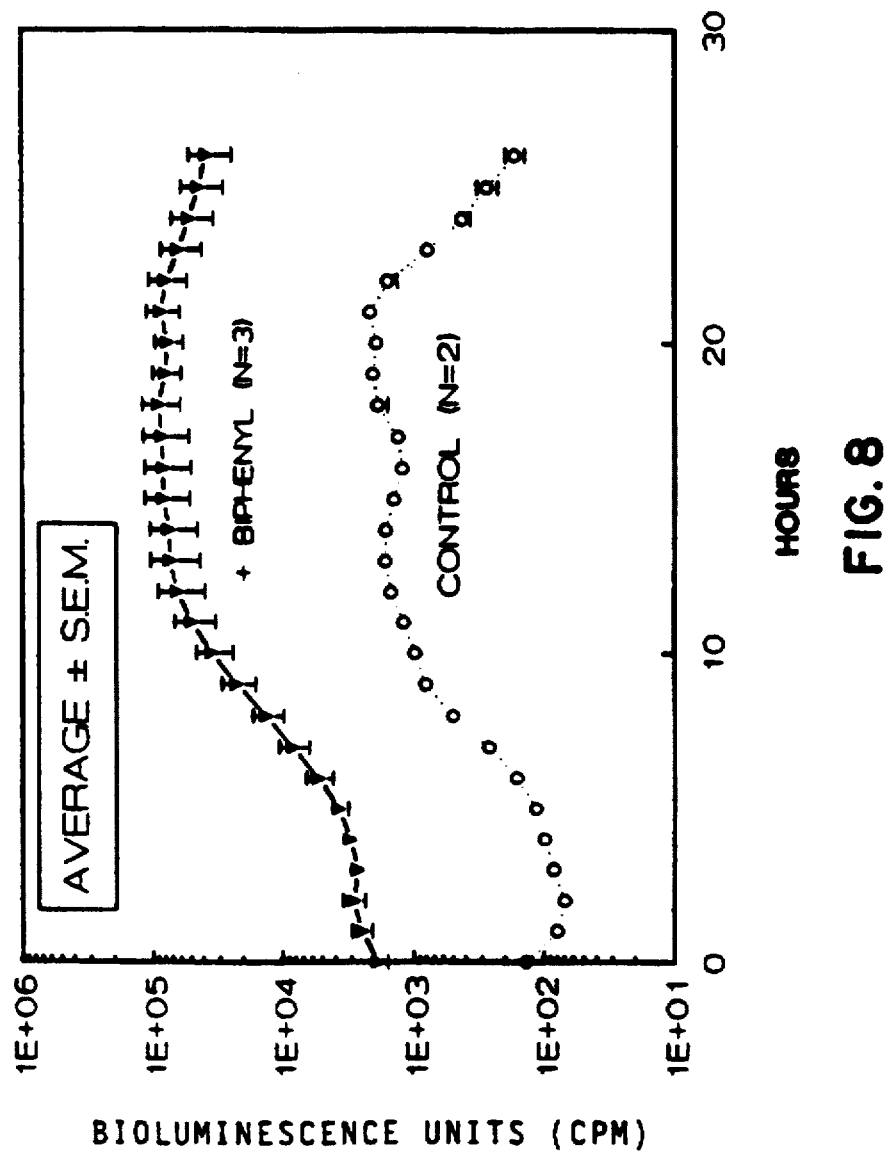

This has been shown for the biphenyl biosensor (FIG. 8).

Biphenyl was used under the solid form. It has also been used in a solution of ethanol, such as the final concentration of biphenyl is between about 10 to about 500 ppm, dissolved in 0.5% (v/v) of ethanol.

Strain A5-23 can also be induced to produce light in the presence of some volatile chlorinated aliphatic solvents (di- and trichloroethane). The common denominator in these compounds and the aromatic inducers, mentioned above, is the presence of Cl atoms in all these molecules.

We claim:

1. A fused gene comprising a promoter sequence derived from a gene of *Alcaligenes eutrophus* strain CH34, SV661, DS185, AE453, or A5, said gene being a regulatory gene involved in the expression of either the resistance to one or several metals or the catabolism of one or several xenobiotic compounds, said promoter from said regulatory gene being an inducible promoter and is inducible in the presence of said metals or xenobiotic compounds, or both, and downstream of the promoter, a five gene lux (CDABE) operon said genes coding for subunit α and β of luciferase, a fatty acid reductase, an acyltransferase and an acylprotein synthase, said operon being under the operational control of said promoter, wherein at least one of said genes produces a detectable signal.

2. The fused gene according to claim 1, comprising the coding sequence of the gene(s) responsible for the resistance to one or several metal(s) or responsible for the catabolism of one or several xenobiotic compound(s).

3. The fused gene according to claim 1, wherein the gene producing a detectable signal:

is either located downstream of the promoter and upstream of the gene encoding the resistance or the catabolism, or is located downstream of the promoter and downstream of the gene encoding the resistance or the catabolism, or is located downstream of the promoter and in the gene encoding the resistance or the catabolism.

4. The fused gene according to claim 1, wherein a termination sequence is located immediately upstream of the promoter.

5. The fused gene according to claim 1, wherein the gene producing a detectable signal is the lux operon originating from *Vibrio fischeri*, from *Vibrio harveyi*, from *Photobacterium phosphoreum*, or from *Xenorhabdus luminescens*.

6. The fused gene according to claim 1, wherein the gene encoding resistance to a metal or encoding the catabolism of a xenobiotic compound originates from bacteria of the *Alcaligenes eutrophus* type.

7. The fused gene according to claim 1, wherein the promoter and the gene encoding resistance is a promoter and a gene encoding resistance to zinc that is obtained from plasmid pBR325 comprising a czc fragment of plasmid pMOL30 from *Alcaligenes eutrophus* strain CH34 and surrounding EcoRI fragment, digested with SalI, said promoter and gene encoding resistance is at the multiple cloning site of the plasmid pUCD615 (in *E. coli* CM600 deposited at the C.N.C.M., Institut Pasteur, 28 rue du Dr Roux, 75015 Paris, on Feb. 28, 1991, under n° I-1050), said plasmid comprising the lux operon of *Vibrio fischeri*.

8. The fused gene according to claim 1, wherein the promoter and the gene encoding resistance is the promoter and gene encoding resistance to cobalt that is obtained from plasmid pBR325 comprising a czc fragment of plasmid pMOL30 from *Alcaligenes eutrophus* strain CH34 digested with EcoRI-PstI, said promoter and gene encoding resistance is at the multiple cloning site of the plasmid pUCD615 (in *E. coli* CM600 deposited at the C.N.C.M., Institut Pasteur, 28 rue du Dr Roux, 75015 Paris, on Feb. 28, 1991, under n° I-1050), said plasmid comprising the lux operon of *Vibrio fischeri*.

9. A recombinant vector, for cloning or expression, comprising a vector sequence, of the type plasmid, cosmid or phage and the fused gene according to claim 1, in one of the nonessential sites for its replication.

10. The recombinant vector according to claim 9, comprising in one of its nonessential sites for its replication, necessary elements to promote, in a cellular host, transcription and translation of the gene producing a detectable signal and transcription of the gene responsible for the resistance to a metal or responsible for the catabolism of a xenobiotic compound.

11. The recombinant vector according to claim 9, comprising necessary elements to promote transcription and translation of the gene responsible for the resistance to a metal or responsible for catabolism of a xenobiotic compound.

12. A cellular host comprising *E. coli* transformed by a recombinant vector according to claim 9 or comprising *Alcaligenes eutrophus* transconjugated by a recombinant vector according to claim 9, and comprising the regulation elements enabling the expression of the gene producing a detectable signal.

13. The cellular host of claim 12, further comprising the regulation elements enabling the expression of the gene encoding resistance to a metal or of the gene encoding the catabolism of a xenobiotic compound.

14. A process for in vitro preparing a bacterial cellular host comprising a fused gene according to claim 1, the process comprising the following steps:

determining the promoter derived from (a) gene(s) of *Alcaligenes eutrophus* and the gene encoding resistance to one or several heavy metals or encoding the catabolism of one or several xenobiotic compound(s);

isolating the corresponding nucleic acid fragment of said promoter and gene;

fusing said nucleic acid fragment with the lux (CDABE) operon deleted from its own promoter;

introducing the result of above-mentioned fusion into a bacterial cellular host; and detecting light producing bacterial cellular host placed in an appropriate medium comprising one or several metal (s) or a xenobiotic compound.

15. The process for in vitro preparing a bacterial cellular host of claim 14, wherein the promoter and the gene encoding resistance to one or several heavy metals or encoding the catabolism of one or several xenobiotic compounds(s) comprises a marker of the presence of the gene;

wherein the lux operon further comprises a marker of the presence of the operon; and wherein the process further comprises selecting the cellular host with the marker(s) placed in a medium where the marker(s) can be detected.

16. The process for in vitro, preparing a bacterial cellular host of claim 15, wherein the promoter is derived from an *Alcaligenes eutrophus* strain comprising CH34, SV661, AE453, DS185, or A5.

17. A process for preparing a bacterial cellular host wherein said bacterial cellular host emits light in the presence of zinc with a detection limit of 1 ppm and dynamic range between 1 and 23 ppm Zinc comprising the steps of:

(a) digesting with SalI a plasmid pBR325 comprising a czc fragment of plasmid pMOL30 from *Alcaligenes eutrophus* strain CH34 and surrounding EcoRI fragment to obtain a promoter and a gene encoding resistance to zinc;

(b) inserting said promoter and said gene encoding resistance to zinc of step (a) into a plasmid pUCD615 (in *E. coli* CM600 deposited at the C.N.C.M., Institut Pasteur, 28 rue du Docteur Roux, 75015 Paris, on Feb. 28, 1991, under No. I-1050), at its multiple cloning site, and comprising the lux operon of *Vibrio fischeri*, to obtain a replicable plasmid;

(c) transforming the replicable plasmid of (b) in *E. coli;*

(d) selecting the inserted plasmid on ampicillin plates with various concentrations of zinc; and (e) detecting the light producing *E. coli* in the presence of zinc.

18. A process for preparing a bacterial cellular host wherein said bacterial cellular host emits light in the presence of cobalt with a detection limit of 1 ppm and dynamic range between 1 and 23 ppm cobalt comprising the steps of:

(a) digesting with SalI a plasmid pBR325 comprising a czc fragment of plasmid pMOL30 from *Alcaligenes eutrophus* strain CH34 and surrounding EcoRI fragment to obtain a promoter and a gene encoding resistance to cobalt;

(b) inserting said promoter and said gene encoding resistance to cobalt of step (a) into a plasmid pUCD615 (in *E. coli* CM600 deposited at the C.N.C.M. Institut Pasteur, 28 rue du Docteur Roux, 75015 Paris, on Feb. 28, 1991, under No. I-1050), at its multiple cloning site, and comprising the lux operon of *Vibrio fischeri*, to obtain a replicable plasmid;

(c) transforming the replicable plasmid of (b) in *E. coli;*

(d) selecting the inserted plasmid on ampicillin plates with various concentrations of cobalt; and (e) detecting the light producing *E. coli* in the presence of cobalt.

19. A process for in vivo preparing a bacterial cellular host comprising a fused gene according to claim 1, comprising the following steps:

conjugating, to obtain transconjugants, a cellular host comprising a promoter derived from *Alcaligenes eutrophus* and a gene encoding the resistance to a metal or encoding the catabolism of a xenobiotic compound with another cellular host comprising a transposon comprising the lux (CDABE) operon without its own promoter;

recovering the transconjugants; and selecting transconjugants emitting light in the presence of a medium containing a metal or a xenobiotic compound.

20. The process for in vivo preparing a bacterial cellular host comprising a fused gene according to claim 19 further comprising the step of:

applying transconjugants to media with different concentrations of metal or xenobiotics.

21. The process for in vivo preparing a bacterial cellular host comprising a fused gene according to claim 19, wherein:

the promoter and gene encoding the resistance to metal or encoding the catabolism of xenobiotic compound further comprises a marker for the presence of the gene;

the transposon comprising lux operon further comprises a marker for the presence of said gene; and the process further comprises selecting transconjugants with the marker(s) placed in a medium where the marker(s) can be detected.

22. The process according to claim 19, wherein:

the bacterial cellular host comprising a promoter and a gene encoding the resistance to a metal is *Alcaligenes eutrophus* and the cellular host comprising a transposon is *E. coli* comprising the vector pUCD623, itself comprising a transposon Tn4431 which is Ty21 transposon comprising the tetracycline resistance and the lux operon of *Vibrio fischeri* without its own promoter, and the process further comprises the steps of:
  selecting the transconjugants on tetracycline plates;
  replicating the transconjugants on media with different concentrations of metals; and
  detecting light producing transconjugants.

23. The process according to claim 22 for preparing a bacterial cellular host emitting light in the presence of chromium with a detection limit of 1 ppm of chromium, wherein the cellular host comprising a promoter and a gene resistant to metal is *Alcaligenes eutrophus* SV661 (deposited at the C.N.C.M., Institut Pasteur, 28 rue du Dr Roux, 75015 Paris, on Feb. 28, 1991, under n° I-1046) and the cellular host comprising the transposon is *E. coli* strain CM601 (deposited at the C.N.C.M., Institut Pasteur, 28 rue du Dr Roux, 75015 Paris, on Feb. 28, 1991, under n° I-1051), which gives strain AE714, transferred into strain A5.3, which is a rifampicin mutant of the biphenyl degrading A5 strain (I-1047), to give strain AE859, which gives light expression in the presence of chromium.

24. The process according to claim 22, for preparing a bacterial cellular host emitting light in the presence of a concentration of at least 1 ppm of nickel, wherein the cellular host comprising a promoter and a gene resistant to a metal is *Alcaligenes eutrophus* AE453 and the cellular host comprising the transposon is *E. coli* strain CM601 (deposited at the C.N.C.M., Institut Pasteur, 28 rue du Dr Roux, 75015 Paris, on Feb. 28, 1991, under n° I-1051), which gives strain AE453 (deposited at the C.N.C.M., Institut Pasteur, 28 rue du Dr Roux, 75015 Paris, on Feb. 28, 1991, under n° I-1049), transferred into strain A5.3, which is a rifampicin mutant of the biphenyl degrading A5 strain (I-1047), to give strain AE891, which gives light expression in the presence of nickel.

25. The process according to claim 22, for preparing a bacterial cellular host emitting light in the presence of copper, wherein the cellular host comprising a promoter and a gene resistant to a metal is *Alcaligenes eutrophus* DS185 (deposited at the C.N.C.M., Institut Pasteur, 28 rue du Dr Roux, 75015 Paris, on Feb. 28, 1991, under n° I-1048), and the cellular host comprising the transposon is *E. coli* strain CM601 (deposited at the C.N.C.M., Institut Pasteur, 28 rue du Dr Roux, 75015 Paris, on Feb. 28, 1991, under n° I-1051), which gives AE866, which gives light expression in the presence of copper.

26. The process according to claim 22, for preparing a bacterial cellular host emitting light in the presence of copper, wherein the cellular host comprising a promoter and a gene resistant to a metal is *Alcaligenes eutrophus* DS310, and the cellular host comprising the transposon is *E. coli* strain CM601 (deposited at the C.N.C.M., Institut Pasteur, 28 rue du Dr Roux, 75015 Paris, on Feb. 28, 1991, under n° I-1051), which gives AE890, which gives light expression in the presence of copper and cannot grow on minimal plates containing lead.

27. The process according to claim 22, for preparing a cellular host emitting light in the presence of biphenyl, wherein the cellular host comprising a promoter and a gene encoding the catabolism of biphenyl compounds is *Alcaligenes eutrophus* A5 (deposited at the C.N.C.M., Institut Pasteur, 28 rue du Dr Roux, 75015 Paris, on Feb. 28, 1991, under n° I-1047), and the cellular host comprising the transposon is *E. coli* strain CM601 (deposited at the C.N.C.M., Institut Pasteur, 28 rue du Dr Roux, 75015 Paris, on Feb. 28, 1991, under n° I-1051), which gives A5.23 or A5.24, which gives light expression in the presence of biphenyl compounds.

28. A cellular host prepared according to the process of claim 15.

29. A cellular host prepared according to the process of claim 19.

30. A process for detecting, in a liquid medium, a metal or a xenobiotic compound in a concentration range of about 1 to about 120 ppm, comprising the steps of:
  placing a cellular host of claim 9 which has been lyophilized and immobilized on a solid support into a liquid medium to form a liquid culture medium;
  introducing a sample of said liquid culture medium containing a cellular host of claim 9 into a sample taken from a liquid medium, in which the presence of a metal or of a xenobiotic compound is to be detected; and
  detecting the signal generated by the presence of said metal or the presence of said xenobiotic compound by detecting means.

31. The process for detecting a metal or xenobiotic compound according to claim 30, wherein the signal is light and the detecting means is a luminometer.

32. A process for detecting, in a liquid medium, a metal or a xenobiotic compound in a concentration range of about 1 to about 120 ppm, comprising the steps of:
  introducing a cellular host of claim 12 contained in a liquid culture medium, into a sample taken from a liquid medium; and
  detecting the signal generated by the presence of said metal or in the presence of xenobiotic compound by detecting means.

33. The process for detecting a metal or xenobiotic compound according to claim 32, wherein the liquid medium is an aqueous medium, the signal is light, and the detecting means is a luminometer.

34. A kit for detecting a metal or xenobiotic compound in a concentration at least about 1 ppm for metals and as little as 1 ppb for xenobiotics, comprising:
  a cellular host of claim 12; and
  detection means to detect the signal generated by the presence of said metal or xenobiotic compound.

35. The kit according to claim 34, wherein the detection means detects light.

* * * * *